(12) United States Patent
Brown et al.

(10) Patent No.: US 11,264,128 B2
(45) Date of Patent: Mar. 1, 2022

(54) MACHINE-LEARNING FRAMEWORK FOR COORDINATING AND OPTIMIZING HEALTHCARE RESOURCE UTILIZATION AND DELIVERY OF HEALTHCARE SERVICES ACROSS AN INTEGRATED HEALTHCARE SYSTEM

(71) Applicant: University Hospitals Cleveland Medical Center, Cleveland, OH (US)

(72) Inventors: Samuel Brown, Chagrin Falls, OH (US); Eric Beck, Bratenahl, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 314 days.

(21) Appl. No.: 16/456,869

(22) Filed: Jun. 28, 2019

(65) Prior Publication Data

US 2020/0411170 A1 Dec. 31, 2020

Related U.S. Application Data

(63) Continuation of application No. 16/456,325, filed on Jun. 28, 2019.

(51) Int. Cl.
*G06Q 10/00* (2012.01)
*G16H 40/20* (2018.01)
(Continued)

(52) U.S. Cl.
CPC .............. *G16H 40/20* (2018.01); *G06N 20/00* (2019.01); *G06Q 10/063114* (2013.01); *G16H 50/20* (2018.01)

(58) Field of Classification Search
CPC .............. G06F 9/5066; G06F 16/2471; G06F 16/24542; G06F 16/24535;
(Continued)

(56) References Cited

U.S. PATENT DOCUMENTS

2014/0114717 A1* 4/2014 Davis ............... G06Q 10/06312
705/7.21
2015/0370974 A1 12/2015 Zebarjadi et al.
(Continued)

OTHER PUBLICATIONS

Non-Final Office Action received for U.S. Appl. No. 16/456,325 dated May 27, 2021, 24 pages.
(Continued)

*Primary Examiner* — Maroun P Kanaan
(74) *Attorney, Agent, or Firm* — Amin, Turocy & Watson, LLP

(57) ABSTRACT

Techniques are described optimizing operations of an integrated healthcare system in real-time using a machine learning framework. In one embodiment, a method comprises monitoring, by a system operatively coupled to a processor, activity of healthcare workers of a healthcare system over a defined timeframe in association with operation of the healthcare system, including monitoring performance of healthcare tasks scheduled for performance over the defined timeframe. The method further comprises determining, by the system based on the monitoring, a timeslot within the defined timeframe in which a healthcare worker of the healthcare workers is not performing, anticipated to perform, or scheduled to perform a healthcare task of the healthcare tasks, and determining, by the system, a supplemental healthcare task for performance by the healthcare worker during the timeslot.

20 Claims, 13 Drawing Sheets

(51) Int. Cl.
*G16H 50/20* (2018.01)
*G06N 20/00* (2019.01)
*G06Q 10/06* (2012.01)

(58) Field of Classification Search
CPC ...... G06F 16/24545; G06F 2209/5017; G06Q 10/06311; G06Q 10/06; G06Q 10/063114; G06Q 10/06398; G06Q 10/063112; G06Q 10/06316; G06Q 10/08355; G06N 20/00; G06N 7/005; G06N 5/003; G16H 40/20; G16H 50/20; G16H 10/60; G16H 10/20; G16H 20/10; G16H 20/00
See application file for complete search history.

(56) References Cited

U.S. PATENT DOCUMENTS

| | | | |
|---|---|---|---|
| 2016/0371620 A1* | 12/2016 | Nascenzi | G06Q 10/06314 |
| 2017/0124526 A1 | 7/2017 | Kumar et al. | |
| 2017/0200101 A1* | 7/2017 | Kumar | G06N 5/003 |
| 2017/0249580 A1 | 8/2017 | Newman et al. | |

OTHER PUBLICATIONS

Letter Restarting Period for Response received for U.S. Appl. No. 16/456,325 dated Sep. 3, 2021, 26 pages.

* cited by examiner

EXAMPLE INDEXED TASK DATA

Time: 9:18 am
Date: April 22, 2019
Location: Hospital A

| Task Identifier | Patient | Status | Timing | | Expected Duration | Location | Priority |
|---|---|---|---|---|---|---|---|
| | | | Origination | Scheduling | | | |
| Clinical 891 | John James | pending | 9:01 | asap | 60 min | Unit A | urgent |
| Clinical 99 | Jennifer Adams | pending | 6:00 | end-of-day | 30 min | Unit A | high |
| Clinical 778 | Erin Cauly | pending | 8:30 | end-of-day | 15 min | Unit A | high |
| Admin 82 | N/A | in-progress | 7:00 | by 1500 | 45 min | Unit N | low |
| Admin 911 | N/A | pending | 7:00 | 1400 fixed | 20 min | N/A | mid |
| Transport 21 | Matthew Arlington | pending | 8:47 | 1200 flex | 10 min | Unit A - C | low |
| Transport 21 | Donna Keller | in-progress | 9:10 | 9:30 | 20 min | Unit C - E | mid |
| EVS 449 | N/A | pending | 7:44 | end-of-day | 30 min | Unit H | high |
| Clinical 145 | Amy Peters | pending | 8:22 | 12:00 | 60 min | Unit B | mid |
| Clinical 98 | Sean Solman | pending | 6:29 | 11:00 fixed | 90 min | Unit B | mid |
| Admin 118 | N/A | in-progress | 8:30 | asap | 15 min | N/A | urgent |
| Admin 119 | N/A | pending | 8:30 | by 1500 | 12 min | Unit P | high |
| Admin 120 | N/A | pending | 8:30 | by 1500 | 15 min | N/A | low |
| EVS 445 | N/A | in-progress | 7:48 | asap | 30 min | Unit H | urgent |
| EVS 446 | N/A | pending | 9:15 | end-of-day | 60 min | Unit D | low |
| EVS 448 | N/A | pending | 9:16 | asap | 60 min | Unit D | mid |

FIG. 4

Time: 9:18
Date: April 22, 2019
Location: Hospital A

EXAMPLE RESOURCE AVAILABILITY DATA

| Name/Identifier | Status | Expected Time Till Available | Expected Duration Available | Location | Mobility State | Fatigue Level |
|---|---|---|---|---|---|---|
| ID #120845 | Available | N/A | 60 min | Unit A | N/A | 1 |
| ID #120301 | Available | N/A | 60 min | Unit A | N/A | 1 |
| ID #134045 | Unavailable | 30 min | 30 min | Unit A | N/A | 3 |
| ID #138928 | Available | N/A | 15 min | Unit N | N/A | 4 |
| ID #122829 | Unavailable | 45 min | 45 min | Unit A | N/A | 2 |
| ID #125505 | Unavailable | 20 min | 20 min | Unit A | N/A | 1 |
| ID #158045 | Available | N/A | 10 min | Unit E | N/A | 5 |
| ID #123052 | Idle | 20 min | 20 min | Unit H - home | Driving | 1 |
| ID #351990 | Available | N/A | 30 min | Unit B | N/A | 2 |
| ID #110898 | Idle | 30 min | 60 min | Unit B | Walking | 4 |
| ID #312086 | Unavailable | 90 min | 90 min | N/A | N/A | 1 |
| ID #391881 | Available | N/A | 15 min | Unit P | N/A | 2 |
| ID #234031 | Idle | 12 min | 12 min | Unit C - F | Walking | 1 |
| ID #302821 | Unavailable | 15 min | 15 min | Unit H | N/A | 5 |
| ID #390193 | Available | N/A | 30 min | Unit D | N/A | 5 |
| ID #293801 | Idle | 15 min | 60 min | Unit D | N/A | 2 |
| ID #129382 | Available | N/A | 60 min | Unit C | N/A | 1 |

EXAMPLE HEALTHCARE WORKER INFORMATION

Name: Dr. Keller
Title: Neurological Surgeon, MD
Primary Location: Hospital A

| Task Type | System Preference Rating | Performance Rating | Compensation Rate | Worker Preference Rating |
|---|---|---|---|---|
| Procedure 832 | 2 | 90% | X/X | 3 |
| Procedure 824 | 1 | 91% | X/X | 2 |
| Procedure 821 | 2 | 95% | Y/X | 1 |
| Procedure 918 | 1 | 86% | Y/X | 1 |
| Procedure 223 | 1 | 88% | X/X | 2 |
| Procedure 221 | 6 | 93% | Z/X | 3 |
| Procedure 228 | 2 | 77% | Z/X | 1 |
| Clinical Task 11 | 4 | 78% | M/X | 4 |
| Clinical Task 12 | 1 | 90% | M/X | 4 |
| Clinical Task 14 | 3 | 76% | M/X | 4 |
| Clinical Task 19 | 5 | 63% | M/X | 5 |
| Admin Task 118 | 3 | 89% | N/X | 3 |
| Admin Task 119 | 5 | 82% | N/X | 4 |
| Admin Task 120 | 6 | 75% | N/X | 5 |
| EVS Task 445 | 8 | 88% | S/X | 8 |
| EVS Task 446 | 5 | 66% | S/X | 8 |
| EVS Task 448 | 7 | 60% | S/X | 9 |

FIG. 8

MACHINE-LEARNING FRAMEWORK FOR COORDINATING AND OPTIMIZING HEALTHCARE RESOURCE UTILIZATION AND DELIVERY OF HEALTHCARE SERVICES ACROSS AN INTEGRATED HEALTHCARE SYSTEM

CROSS-REFERENCE TO RELATED APPLICATIONS

This application is a continuation of and claims the benefit of priority to U.S. patent application Ser. No. 16/456,325 filed Jun. 28, 2019 and titled "MACHINE-LEARNING FRAMEWORK FOR COORDINATING AND OPTIMIZING HEALTHCARE RESOURCE UTILIZATION AND DELIVERY OF HEALTHCARE SERVICES ACROSS AN INTEGRATED HEALTHCARE SYSTEM," the entirety of which application is hereby incorporated herein by reference.

TECHNICAL FIELD

This application relates to computer-implemented techniques for coordinating and optimizing healthcare resource utilization and delivery of healthcare services across an integrated healthcare system using a machine learning framework.

BACKGROUND

The predominant form of health care available in the United States is fragmented care, provided by atomistic, unconnected physician practices and a culture of physician autonomy, hospitals, and other providers. Fragmentation in healthcare delivery refers to the systemic misalignment of incentives or lack of coordination among providers that results in inefficient allocation of resources in a manner that hinders patient care. For example, today, an individual must make the decision to seek medical advice or attention with little or no guidance as to how and where to initiate receiving the appropriate care based on the patient's assumed medical need. While advice may be sought through a friend or family member or searching the Internet, entry into the formal healthcare ecosystem is dependent on the available capacity at each entry point and is not coordinated across multiple sites or modalities.

Once an initial consultation or assessment is performed by a credentialed healthcare provider (entry point), a plan of action is generally developed that involves a series of recommended actions or services to be rendered to the individual before re-assessment is completed and additional actions or services are prescribed. This cycle of assessment and assignment or prescription of actions or services to be rendered may be repeated multiple times. However, each of these actions or services are facilitated or rendered by disparate, uncoordinated, operating entities which are composed of siloed people, processes, and technology. Each operating entity has a finite amount of capacity that makes up their available capacity to render various levels of service or activities. As a result, the individual seeking these services or activities is reliant on each individual operating entity's specifically assigned resources dictating available capacity with little or no regard to the specific needs and preferences of the individual. Never are all operating entities and patients coordinated in a meaningful fashion to deliver optimal operating efficiency utilizing all available resources in a network to drive an optimized, and patient specific experience according to patient preference.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are described that provide for coordinating and optimizing healthcare resource utilization and delivery of healthcare services across an integrated healthcare system using a machine learning framework.

According to an embodiment, a system is provided that comprises a memory that stores computer executable components, and a processor that executes the computer executable components stored in the memory. The computer executable components can comprise a task information extraction component that receives information identifying currently pending healthcare tasks for performance by healthcare workers of a healthcare system. The computer executable components further comprise an activity monitoring component that monitors activity of the healthcare workers in association with operation of the healthcare system, and an availability analysis component that determines availability information regarding current availability of respective healthcare workers of the healthcare workers to perform the currently pending tasks based on the activity information. The computer executable components further comprise a task optimization analysis component that determines a task assignment scheme that assigns one or more of the healthcare workers to the currently pending tasks in a manner that minimizes a total amount of delay between timing of origination of the currently pending tasks and timing of initiation of performance of the currently pending tasks based on the availability information.

In one or more embodiments, the availability information indicates durations of time until respective healthcare workers of the healthcare workers can initiate the performance of the currently pending tasks. In some implementations, the availability analysis component determines the durations of time based on locations of the respective healthcare workers and task locations of the respective tasks. The availability analysis component can also determine the availability information based on known scheduling information regarding known or expected times or timeframes in which the respective healthcare workers will be unavailable (e.g., off-schedule or otherwise performing a task), based on expected durations of time to complete tasks underway, based on current operating conditions of the healthcare system and the like. In various embodiments, the availability analysis component can employ machine learning and artificial intelligence to facilitate determining the availability information (e.g., using one or more models developed/trained based on historical activity information for the healthcare workers and historical performance of the healthcare tasks under various operating conditions/contexts of the healthcare system).

In some implementations, the task optimization analysis component further determines the task assignment scheme based on defined worker capability information for the respective healthcare workers and defined capability requirements of respective healthcare tasks of the currently pending task. With these implementations, the computer executable components further comprise a filtering component that identifies subsets of the healthcare workers capable or credentialed to perform the respective healthcare tasks based on the defined worker capability information and the defined capability requirements, and wherein the task optimization analysis component restricts assignment of the one or more healthcare workers to the currently pending tasks based on the subsets. For example, the defined worker capability information can identify different types of healthcare tasks the respective healthcare workers are capable of performing. The defined worker capability information can also comprise preference classifications for the different types of healthcare tasks representative of relative preference for performance of the different types of healthcare tasks by the respective healthcare workers, and wherein the task optimization analysis component further determines the task assignment scheme based on the preference classifications. In some implementations, the task optimization analysis component further determines the task assignment scheme using an optimization function that favors respective healthcare tasks of the currently pending healthcare tasks to primary healthcare workers of the healthcare workers that have a higher preference classification for the currently pending tasks relative to secondary healthcare workers of the healthcare workers that have a lower preference classification for the currently pending tasks based on respective types of the currently pending tasks.

The task optimization analysis component can also be configured to determine the task assignment scheme based on priority information associated with respective tasks of the currently pending tasks that identifies priority levels of the respective tasks. The task optimization analysis component can also evaluate costs associated with different task assignment schemes that assign the one or more healthcare workers to the currently pending tasks in different manners and selects the task assignment scheme based on the task assignment scheme minimizing the costs. For example, the costs can include financial costs attributed to time delays, attributed to compensation schemes associated with using certain workers for certain tasks, attributed to expected clinical complications or losses attributed to using certain workers for certain tasks, costs attributed to failure to meet defined regulatory requirements/protocols associated with performing the respective tasks (e.g., by a qualified healthcare worker, in a minimum timeframe, etc.) and the like. In some embodiments, the currently pending healthcare tasks involve provision of healthcare to a patient, and wherein the task optimization analysis component determines the task assignment scheme based on one or more preferences of the patient.

In various embodiments, the task optimization analysis component further determines the task assignment scheme using one or more machine learning task optimization models configured to infer optimal tasks for performance by the healthcare workers based on analysis of historical operations data regarding historical performance of various healthcare tasks by the healthcare workers under different operating conditions of the healthcare system. The computer executable components can also comprise a task forecasting component that forecasts upcoming need of the respective healthcare workers in association with performance of future tasks of the healthcare system within a defined, upcoming timeframe, and wherein the task assignment component further determines the task assignment scheme based on the upcoming need.

In another embodiment, another system is provided that comprises a memory that stores computer executable components, and a processor that executes the computer executable components stored in the memory. The computer executable components can comprise an activity monitoring component that monitors activity of healthcare workers of a healthcare system over a defined time period in association with operation of the healthcare system, including monitoring performance of healthcare tasks scheduled for performance over the defined time period. The computer executable components further comprise a availability analysis component that determines, based on the monitoring, a timeslot within the defined time period in which a healthcare worker of the healthcare workers is not performing, anticipated to or scheduled to perform a healthcare task of the healthcare tasks, and a task optimization analysis component that determines a supplemental healthcare task for performance by the healthcare worker during the timeslot.

In some embodiments, the computer executable components further comprise a task assignment component that generates and sends a task assignment message to a device associated with the healthcare worker comprising information that recommends the healthcare worker perform the supplemental healthcare task during the timeslot. In one implementation of these embodiments, the computer executable components further comprise a task compensation evaluation component that determines a monetary compensation value for performance of the supplemental healthcare task by the healthcare worker based on a qualification of the healthcare worker, a type of the task, and an expected duration of the task, and wherein the task assignment message comprises information identifying the monetary compensation value. In various implementations, the supplemental task comprises a telemedicine service, and wherein the task assignment component includes a link associated with the telemedicine service, wherein selection of the link facilitates performance of the telemedicine service using the device.

The computer executable components can further comprise a location tracking component that receives location and movement data regarding locations and movement of the healthcare workers in real-time over the defined time period, and wherein the task monitoring component determines the timeslot based on the location and movement data. In one implementation, the timeslot comprises a traveling timeslot over which the healthcare worker will travel from a first location to a second location, and wherein the task optimization analysis component determines the supplemental task based on a mode the travel. In some embodiments, the availability analysis component further determines, based on the monitoring, one or more segments of idle time associated with a current healthcare task of the healthcare tasks that is currently being performed by the healthcare worker, and wherein the task optimization analysis component determines another supplemental healthcare task for performance by the healthcare worker during the one or more segments of idle time. For example, the idle time can include a time associated with a healthcare task that be used to multitask, such as time between seeing patients, time while waiting for laboratory results, and the like, in which the healthcare worker can perform a telemedicine task or review documents using mobile device.

In some embodiments, the task optimization analysis component can also determine the supplemental healthcare task based on a location of the healthcare worker and a duration of the timeslot. The task optimization analysis component can also determine the supplemental healthcare task based on a current operating context of the healthcare system. In another implementation in which the supplemental healthcare task involves provision of healthcare to a patient, the task optimization analysis component can also determine the supplemental healthcare task for performance by the healthcare worker based on one or more preferences of the patient. The task optimization analysis component can also determine the supplemental healthcare task based on one or more preferences of the healthcare worker. In various implementations, the task optimization analysis component can determine the supplemental healthcare task using one or more machine learning task optimization models configured to infer optimal tasks for performance by the healthcare workers based on analysis of historical operations data regarding historical performance of various healthcare tasks by the healthcare workers under different operating conditions of the healthcare system.

In some embodiments, elements described in the disclosed systems can be embodied in different forms such as a computer-implemented method, a computer program product, or another form.

DESCRIPTION OF THE DRAWINGS

FIG. 4 presents example indexed task data generated by the task assessment module in accordance with one or more embodiments of the disclosed subject matter.

FIG. 6 presents example resource availability data regarding availability of resources of an integrated healthcare system in accordance with one or more embodiments of the disclosed subject matter.

FIG. 8 presents example healthcare worker information that facilitates assigning the healthcare workers to healthcare tasks of an integrated healthcare system in accordance with one or more embodiments of the disclosed subject matter.

DETAILED DESCRIPTION

Figure 1:
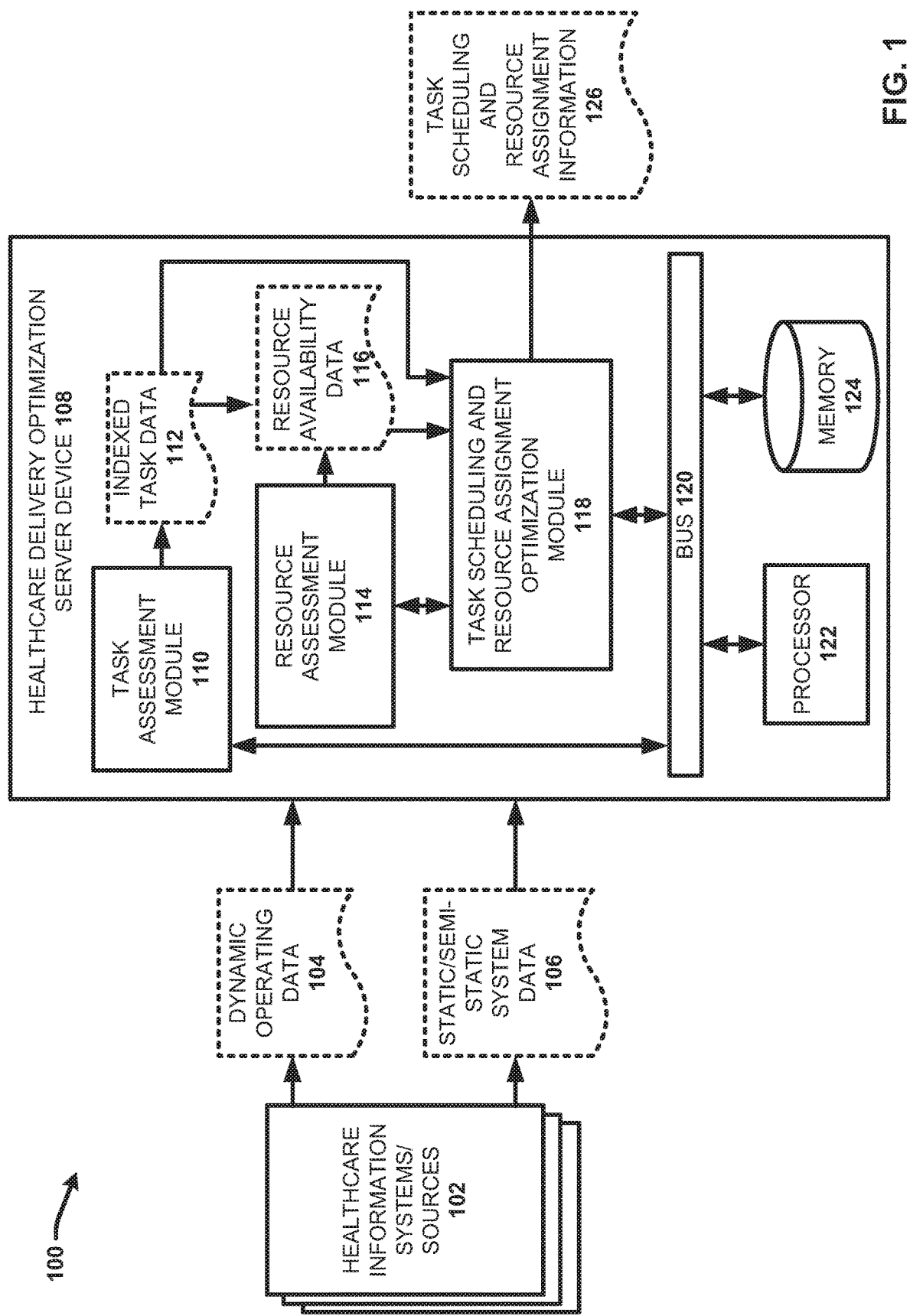
FIG. 1 illustrates a block diagram of an example, non-limiting system for coordinating and optimizing resource utilization and delivery of healthcare services across an integrated healthcare system using a machine learning framework, in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

The disclosed subject matter is directed to systems, computer-implemented methods, apparatus and/or computer program products that provide facilitate coordinating and optimizing resource utilization and delivery of healthcare services across an integrated healthcare system using a machine learning framework. An integrated health care delivery system is one in which all the providers whose services affect a patient work together in a coordinated fashion, sharing relevant medical information, sharing aims or goals, sharing responsibility for patient outcomes, and for resource use. For example, an integrated healthcare system can include many different operating entities that provide a variety of different healthcare services to patients, including hospitals, specialized hospital units, specialized physician clinics/offices, outpatient facilities, ambulatory services, nursing home facilities, surgery centers, imaging/diagnostic providers, pharmacy providers, traveling/in-home patient care, rehabilitation providers, telemedicine providers, and the like.

Various embodiments of the disclosed subject matter provide systems, methods and computer readable media that enable an integrated delivery system using a team-based approach to deliver healthcare services to patients across various patient care settings (e.g., inpatient, outpatient, home, doctor's office, telemedicine/virtual, etc.), balancing and coordinating all patient's needs, available operating entity capabilities and resources in real-time and space. The disclosed techniques are based on multi-dimensional care delivery model that optimizes care delivery and distribution of resources account for factors in several dimensions, including an operating entity dimension, a patient dimension and a location and time dimension. The operating entity dimension involves monitoring real-time demand for each individual operating entity and intelligently matching the necessary system wide resources to achieve optimal throughput. The components for each discrete service or activity are catalogued whether it be human labor, supplies, equipment, or technology. As demand ebbs and flows, the disclosed techniques can dynamically flex resources across multiple service lines according to skill and attribution.

The second dimension of this model is the discrete patient that has a prescribed number of activities or services to be rendered. Taking into account unique patient's acuity or need, list of discrete services or activities to be completed, and any requires sequencing, the disclosed techniques can determine how to schedule the patient for service to optimize the time required to complete all activities. This sequencing can take taking into account the scheduled steps progress, anticipated date/time of service, the patient's physical location, required travel time/distance, and the overall patient's available time window to have these services rendered. A third dimension is space and time. In this regard, the disclosed techniques further balancing the operating entity dimension with the patient dimension in real-time with the variables of time and space. As a result, the entire system can be optimized to deliver improved operating entity performance while also improving patient movement through prescribed services and actions.

With this operating model in mind, various embodiments described herein provide a system is provided that can facilitate optimizing scheduling of different healthcare tasks and assigning resources to the different healthcare tasks in real-time in a manner that synchronizes and harmonizes patient needs and provider capabilities under the dynamic operating conditions associated with the healthcare environment. The healthcare environment can include individual operating entities, as well as a macro ecosystem that combines the individual operating entities into a unified integrated healthcare system. For example, the operating entities can include various types of healthcare facilities that provide healthcare services, including (but not limited to), hospitals, clinics, ambulatory surgical centers, birth centers, blood banks, specialty clinics or medical offices, dialysis centers, hospice homes, imaging and radiology centers, therapy centers, mental health treatment centers, nursing homes, orthopedic and other rehabilitation centers, urgent care facilities, and the like.

In one or more embodiments, the system collects and combines real-time and historical data from various integrated healthcare provider systems and sources regarding patient needs and all aspects of operations of the different healthcare providers that are available to provide healthcare services to patients. In this regard, the system can access and retrieve or receive operating information from different operating entities in real-time over a course of operating of the one or more operating entities regarding what task needs to be done (e.g., clinical tasks and non-clinical task for performance by a wide range of clinicians, healthcare workers and the like, when and where within the healthcare system at a current point in time and/or over a defined, upcoming period of time. The system can further extract and receive up-to-date information from the different operating entities regarding who or whom is available to perform the tasks, and who is the best person/persons to perform the tasks. The system can further evaluate the information using various machine learning models and/or optimization models/algorithms to determine how to schedule performance of the tasks with respect to time and location and how to assign resources (e.g., workers and optionally non-human resources) to the tasks in a manner that results in performing the tasks in the most efficient and effective manner, using the right resources at the right time for the right patient in the right place. For example, the system can determine how to optimize the operations of individual operating entities with respect to scheduling and managing performance of all healthcare tasks at the individual operating entities in a manner that results in the most efficient and effective utilization of available system resources while accounting for the collective and personal needs and preferences of all patients. Using similar machine learning and optimization techniques, the system can further determine how to optimize the operations of the different operating entities as a whole to achieve even greater efficiency in terms of resource utilization while providing patients more personalized and timely access to appropriate clinical care by coordinating and synchronizing patient and provider needs leveraging shared resources.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 for coordinating and optimizing healthcare resource utilization and delivery of healthcare services across an integrated healthcare system using a machine learning framework, in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, in the embodiment shown, system 100 includes a healthcare delivery optimization server device 108 and a plurality of healthcare information systems/sources 102. The healthcare delivery optimization server device 108 can include various computer executable components, including but not limited to, a task assessment module 110, a resource assessment module 112 and a task scheduling and resource assignment optimization module 118. The healthcare delivery optimization server device 108 can include or be operatively coupled to at least one memory 124 and at least one processor 122. The at least one memory 124 can store executable instructions (e.g., the task assessment module 110, the resources assessment module 114, and the task scheduling and resource assignment optimization module 118) that when executed by the at least one processor 122, facilitate performance of operations defined by the executable instructions. In some embodiments, the memory 124 can also store one or more of the various data sources and/or data structures of system 100 (e.g., the healthcare information systems/sources 102, the dynamic operating data 104, the static/semi-static system data 106, the indexed task data 112, the resource availability data 116, and the task scheduling and resource assignment information 126). In other embodiments, one or more of the various data sources and/or data structures of system 100 can be stored in other memory (e.g., at a remote device or system), that is accessible to the healthcare delivery optimization server device 108 (e.g., via one or more networks). The healthcare delivery optimization server device 108 can further include a device bus 120 that communicatively couples the various components and data sources of the healthcare delivery optimization server device 108 (e.g., the task assessment module 110, the resources assessment module 114, the task scheduling and resource assignment optimization module 118, the processor 122, and the memory 124). Examples of said processor 122 and memory 124, as well as other suitable computer or computing-based elements, can be found with reference to FIG. 12, and can be used in connection with implementing one or more of the systems or components shown and described in connection with FIG. 1 or other figures disclosed herein.

Although system 100 co-locates the task assessment module 110, the resource assessment module 114 and the task scheduling and resources assignment optimization module 118 at a same device (e.g., the healthcare delivery optimization server device 108), it should be appreciated that these modules and/or one or more components of these modules (discussed in greater detail infra) can be provided in a distributed manner across various interconnected (via one or more networks) systems and devices (e.g., internal systems, the cloud, two or more dedicated servers, etc.). In this regard, the healthcare delivery optimization server device 108 can be or correspond to a distributed computing system including a network of interconnected devices (e.g., back-end servers, front-end servers, dedicated machines, virtual machines, client devices, etc.), machine, databases, datastores and the like.

In this regard, in some implementations, the healthcare delivery optimization server device 108, one or more of the various modules (and associated components), and/or one or more of the various data sources/structures of system 100 (and other systems described herein) can be communicatively connected via one or more networks. Such networks can include wired and wireless networks, including but not limited to, a cellular network, a wide area network (WAD, e.g., the Internet) or a local area network (LAN). For example, the healthcare delivery optimization server device 108 can communicate with the healthcare information sources/systems 102 using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. The computing device 108 can thus include hardware (e.g., a central processing unit (CPU), a transceiver, a decoder), software (e.g., a set of threads, a set of processes, software in execution) or a combination of hardware and software that facilitates communicating information between the healthcare delivery optimization server device 108 and externals systems, sources and devices.

The healthcare delivery optimization server device 108 can provide various features and functionalities that facilitate optimizing utilization of healthcare resources and delivery of healthcare services. In one or more embodiments, the healthcare delivery optimization server device 108 can facilitate optimizing scheduling of different healthcare tasks and assigning resources to the different healthcare tasks in real-time in a manner that synchronizes and harmonizes patient needs and provider capabilities under the dynamic operating conditions associated with the healthcare environment. The healthcare environment can include individual operating entities, as well as a macro ecosystem that combines the individual operating entities into a unified integrated healthcare system. For example, the operating entities can include various types of healthcare facilities that provide healthcare services, including (but not limited to), hospitals, clinics, ambulatory surgical centers, birth centers, blood banks, specialty clinics or medical offices, dialysis centers, hospice homes, imaging and radiology centers, therapy centers, mental health treatment centers, nursing homes, orthopedic and other rehabilitation centers, urgent care facilities, and the like. The operating entities can also include healthcare entities that provide mobile or in-home care services patients (e.g., traveling nurses, emergency medical services). The operating entities can also include entities that provide virtual or telemedicine services, such as remote monitoring services, virtual radiology services, remote clinical services (e.g., consolations, diagnostic appointments, check-ups, question and answer sessions, mental health sessions, etc.) delivered via phone and/or video conferencing, and the like. In some implementations, the operating entities can also include information technology systems that provide and/or execute medical software products used in association with clinical workflows.

In the embodiment shown, the healthcare information systems/sources 102 can include a variety of electronic data sources and/or systems associated with one or more operating entities of a healthcare system (e.g., an integrated healthcare system) that employs the features and functionalities of the healthcare delivery optimization server device 108. The healthcare information sources/systems 102 can provide a variety of dynamic operating data 104 and static/semi-static system data 106 associated with the respective operating entities that can be used by the healthcare delivery optimization server device 108 as input for various machine learning and/or statistical models configured to generate inferences/determinations in real-time regarding how to optimize utilization of available healthcare resources and delivery of healthcare services by the respective operating entities over a course of operation of the respective operating entities.

In this regard, the dynamic operating data 104 can include information regarding operating conditions of a healthcare operating entity (e.g., a hospital, a surgery centers, a nursing home, etc.) that constantly or regularly change over relatively short timeframes during a course of operation of a healthcare operating entity (e.g., by the second, by the minute, by the hour, by the day, etc.). For example, the dynamic operating data 104 can include information provided by patient scheduling systems, patient monitoring systems, patient tracking systems, operational data logging systems, workflow tracking systems, resource tracking/monitoring systems, and the like. In one or more implementations, the dynamic operating data 104 can include various types of information for each individual operating entity that identifies or indicates the various healthcare tasks that are needed for performance by/at the operating entity at a current point in time/or over a defined, upcoming timeframe (e.g., the current workday, the next 24 hours, the next week, the next month, etc.) to account for known and optionally forecasted patient needs at the current point in time and over. The dynamic operating data 104 can also include information regarding the state, status/condition, availability, movement, location, and other dynamic parameters associated with the healthcare resources that are needed to perform the healthcare tasks and/or the patient associated with the healthcare task.

In this regard, the term healthcare task as used herein can include essentially any defined (predefined or defined by the task assessment module 110) task involved in a course of patient care that is provided by and/or controlled by one or more individuals that are associated with the operating entity or entities involved in the course of patient care. The one or more individuals can include employees/staff, volunteers, independent contractors, patients, and/or patient aids (e.g., a friend or family member of the patient, a personal assistant/aid of the patient, etc.). For example, the healthcare tasks can include clinical tasks, clerical tasks, administrative tasks, environmental services tasks and the like, performed by and/or facilitated by clinicians, physicians, nurses, pharmacists, social workers, therapists, emergency services clinicians/technicians, community health workers, transportation workers, care coordinators, law enforcement, complimentary/alternative medicine practitioners, behavioral health workers, environmental services workers, food service workers, and the like. In some implementations, the healthcare tasks can include non-clinical tasks, such as tasks involving transporting patients and/or supplies, EVS tasks, task involving equipment/technology repair and maintenance, administrative tasks (e.g., verifying insurance qualifications, obtaining authorization for procedures, etc.), and the like. Although various embodiments are described with the assumption that the one or more individuals include humans, in some implementations, the one or more individuals can include machines that are configured to perform certain healthcare tasks autonomously and/or at the control of a human (e.g., intelligent machines, robots, self-driving vehicles, etc.). The term healthcare worker is used herein to refer to any individual or machine associated with an operating entity that can perform a healthcare task.

The static/semi-static system data 106 can include information associated with the respective operating entities, employees of the operating entities, and patients that does not change over time and/or may change at a relatively infrequent rate compared to the dynamic operating data 106. For example, the static/semi-static system data can include information stored one or more databases regarding defined system protocols, regulations, operating requirements, employee administrative information, patient electronic health records (EHRs), patient imaging studies, patient laboratory studies, clinical orders/notes, patient preference information, employee performance records and the like. Additional details regarding the healthcare information systems/sources 102 and the types of dynamic operating data 104 and static/semi-static system data 106 that can be used by the healthcare delivery optimization server device 108 are described in greater detail infra with reference to FIG. 2.

In various embodiments, the healthcare delivery optimization server device 108 can access and retrieve or receive dynamic operating data 104 and static/semi-static system data 104 for one or more operating entities (e.g., operating entities of an integrated healthcare system) in real-time over a course of operating of the one or more operating entities. In some implementations, the healthcare delivery optimization server device 108 can also access, retrieve and/or collect historical sets of the dynamic operating data 104 and corresponding static/semi-static system data 106 (e.g., for developing, training and/or tuning one or more machine learning optimization models employ by the healthcare delivery optimization server device 108, as discussed in greater detail infra). The healthcare delivery optimization server device 108 can further evaluate the dynamic operating data 104 and the static/semi-static system data 106 using various machine learning models and/or optimization models/algorithms to determine how to optimize the operations of individual operating entities with respect to scheduling and managing performance of all healthcare tasks at the individual operating entities in a manner that results in the most efficient and effective utilization of available system resources while accounting for the collective and personal needs and preferences of all patients. Using similar machine learning and optimization techniques, the healthcare delivery optimization server device 108 can further determine how to optimize the operations of the different operating entities as a whole to achieve even greater efficiency in terms of resource utilization while providing patients more personalized and timely access to appropriate clinical care by coordinating and synchronizing patient and provider needs leveraging shared resources.

The various features and functionalities of the healthcare delivery optimization server device 108 can be dived into three components, including a task assessment component performed by the task assessment module 110, a resources assessment component performed by the resource assessment module 114, and a task scheduling and resource assignment optimization component performed by the task scheduling and resource assignment optimization module 118.

The task assessment component involves the extraction, evaluation and indexing of information from the healthcare information systems/sources 102 regarding healthcare tasks performed, being performed, scheduled for performance and/or anticipated (forecasted) for performance by respective operating entities included in the integrated healthcare system. In this regard, the task assessment module 110 can extract information from various information systems/sources (e.g., the healthcare information systems/sources 102) associated with the respective operating entities regarding all (or grouped subset of) the various healthcare tasks that need to be performed by the respective operating entities from a current point in time and into a defined, upcoming timeframe (e.g., the workday, the next hour, the next 24 hours, the next week, the next month etc.) to satisfy all (or a grouped subset) current and future (e.g., known or forecasted) patient needs. The task assessment module 110 can further evaluate the task information to identify discrete healthcare tasks associated with each patient represented in the extracted data. For example, the task assessment module 110 can evaluate information for a patient identifying or indicating scheduled procedures, appointments and check-ups, identifying clinical orders, defining a prescribed care plan, defining a medication regimen, defining a feeding regimen, tracking patient status, identifying patient transfer needs (including current and destination location of the patient), providing real-time feedback requesting or indicating immediate or future medical care (e.g., provided by the patient, gathered indirectly via a patient monitoring system), and the like. Based on evaluating this information, the task assessment module 110 can identify discrete healthcare tasks for performance by one or more healthcare workers to satisfy the patient's needs and/or that are required for provision to the patient based on defined protocols, regulations, requirements, service level agreements (SLA)s, etc., of the operating entity or entities responsible for the patient.

The task assessment module 110 can further determine and associate attribute information with each discrete task regarding constraints, conditions and/or requirements that can influence if the task is performed (e.g., based on authorization restrictions, necessity etc.), when the task is performed, where the task is performed, how the task is performed (e.g., in person, using telemedicine), who or whom performs the task (e.g., a person or person), and/or what additional (non-human) resources are used (e.g., supplies, instruments, equipment, technology, etc.). For example, the task assessment module 110 can determine and associate attribute information with each task that identifies a defined type or classification of the task (e.g., determined based on predefined task classification/type coding system), a time of origination of the task, a time or time frame for completing the task, an expected duration of the task, a location associated with the task, a priority level associated with the task, an and the like. The task assessment module 110 can also determine and associate information with a task that indicates patient preference regarding when, where, by whom and/or how the task is performed. In some embodiments, the task assessment module 110 can also evaluate tasks associated with a single patient or different patient to identify and associate dependency information with the respective tasks regarding dependencies between two or more tasks, such as dependencies that restrict or control order of performance of the tasks, and/or that restrict or control performance of the tasks by a same healthcare worker or healthcare team (e.g., including two or more healthcare workers). The task assessment module 110 can also determine and associate resource attributes with the healthcare tasks that identify or indicate requirements for resources to be used for the tasks, including requirements for healthcare workers authorized to perform the tasks (e.g., based on credentials, job description, performance levels, fatigue levels, etc.), as well as requirements for non-human resources, such as required medications, medical supplies, devices, equipment, technology and the like for use in association with performing the respective tasks.

The task assessment module 110 can further generate indexed task data 112 that comprises one or more data structures that organizes and indexes task information regarding all the discrete tasks, their associated attributes and/or interdependencies. The task assessment module 110 can further regularly and/or continuously update the indexed task data 112 in real-time over the course of operation the integrated healthcare system to reflect changes to the integrated healthcare system. For example, the task assessment module 110 can regularly and/or continuously update the indexed task data to reflect progress of performance and completion of the tasks, to reflect newly added tasks, to reflect changes in operating conditions that effect one or more attributes of the tasks, and the like. In this regard, the indexed tasks data 112 can be or correspond to a dynamic monitor of what healthcare tasks should/could be done to take care of all current (and optionally forecasted) patient needs from a current point in time and into the future (to a defined time point in the future), while also providing relevant information that can influence when, where, how, and by whom the healthcare tasks are performed to optimize utilization of available system resources while also accounting for patient needs and preferences.

Figure 3:
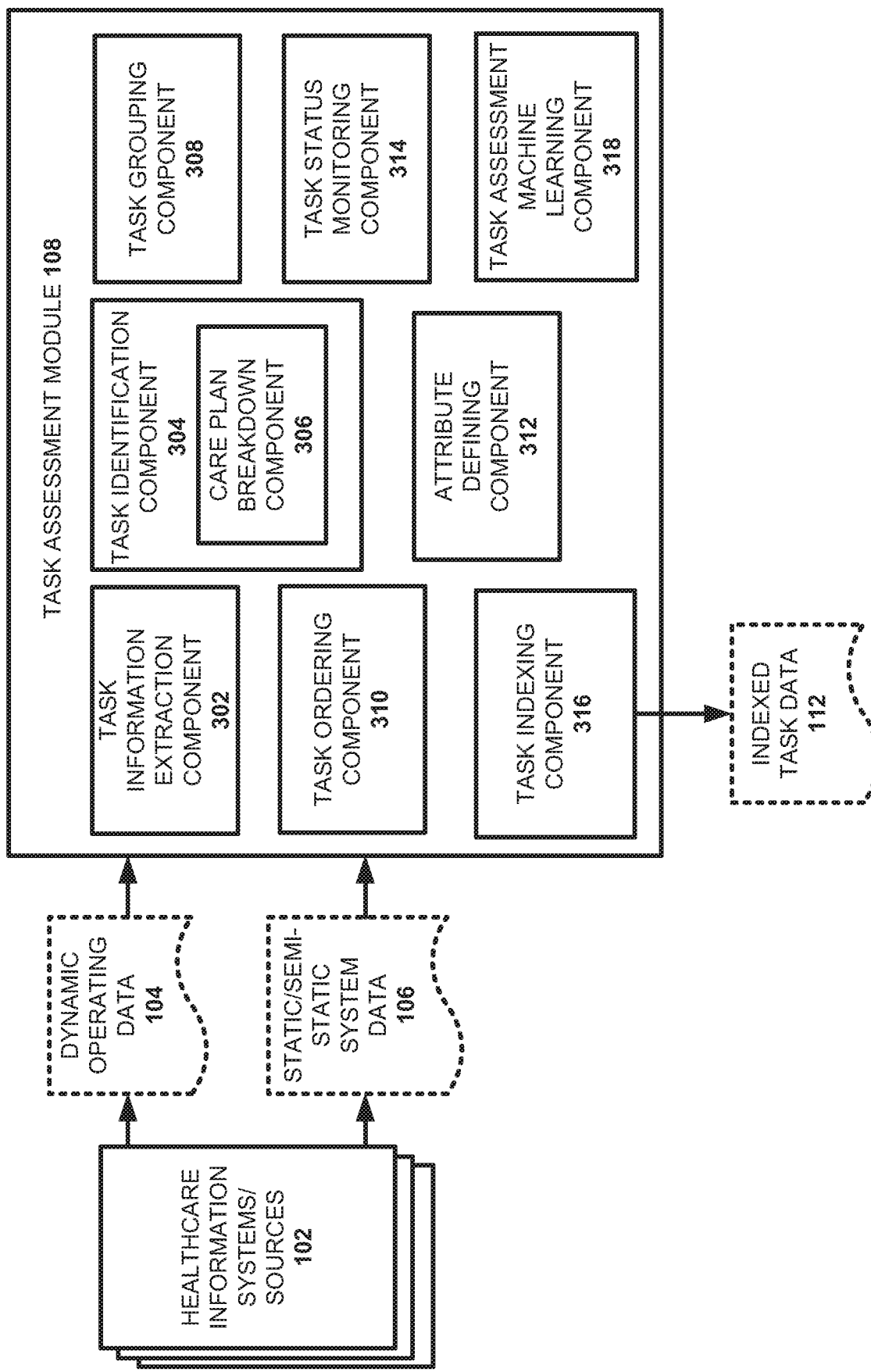
FIG. 3 presents an example task assessment module that facilitates determining information regarding currently pending and forecasted healthcare tasks for performance by one or more operating entities of an integrated healthcare system in accordance with one or more embodiments of the disclosed subject matter.

Additional details regarding the features and functionalities of the task assessment module 110 are discussed in greater detail infra with reference to FIG. 3.

The resource assessment component involves the extraction and evaluation of information from the healthcare information systems/sources 102 regarding the availability of resources of the one or more operating entities to perform the currently pending and upcoming healthcare tasks. In various embodiments, the resources of interest are the individuals (e.g., manual resources) that can perform the healthcare tasks (e.g., the doctors, nurses, therapists, aids, technicians, transportation workers, food service workers, ambulatory technicians, paramedics, etc.), collectively referred to herein as healthcare workers. In this regard, the resource assessment module 114 can be configured to extract and evaluate the dynamic operating data 104 regarding the activity of the various healthcare workers in real-time in view of any scheduling constraints for the healthcare workers to determine resource availability data 116 regarding availability of the respective healthcare workers to perform currently pending tasks and/or upcoming tasks (e.g., known, scheduled, and/or forecasted). The resource assessment module 114 can further determine and generate resource availability data 116 that identifies the respective healthcare workers (e.g., by name or another resource identification number) and provides information regarding the availability of the respective workers at a current point in time and/or over a defined, upcoming timeframe (e.g., the workday, the workweek, the next hour, the next 24 hours, the next month, etc.).

For example, the resource availability data 116 can include but is not limited to, information that identifies a current availability status of the healthcare workers (e.g., available, unavailable), that identifies or indicates durations of time until the respective workers will become available to perform a healthcare task (e.g., available now, available between hours 1400 and 1500, available in 30 minutes), amount of time the respective workers have available to perform certain tasks (e.g., based on scheduling constraints, shift end time, etc.), and locations of the respective healthcare workers. In some embodiments, the resource availability data 116 can include information that identifies known or expected timeslots over a defined upcoming timeframe (e.g., the next 24 hours, the next week, the next month, etc.) in which one or more healthcare workers have available to perform healthcare tasks, including durations of the timeslots and in some implementations, locations associated with the time slots (e.g., a specific office location). In some embodiments, the resource availability data 116 can further identify available time that the resource assessment module 114 classifies as idle time. As discussed in greater detail infra, idle time can include time in which a healthcare worker is between tasks, traveling (e.g., driving, walking, riding as a passenger, etc.), eating lunch, waiting for laboratory results, or the like, that can be utilized to perform supplementary healthcare tasks, such as telemedicine tasks. In some embodiments, the resource availability data 116 can also include information regarding a physiological state of the healthcare workers (e.g., fatigue level, stress level, intoxication level, etc.) that can be used to facilitate determining if a particular healthcare worker is in a suitable state to perform certain healthcare tasks of the respective workers, and the like.

For example, in one or more embodiments, the resource assessment module 114 can receive dynamic operating data 104 that tracks or facilitates tracking performance of healthcare tasks by the respective healthcare workers in real-time, such as information regarding if a healthcare worker is currently performing a healthcare task, what tasks respective healthcare workers are currently performing, scheduled tasks the respective workers are scheduled to perform (including where and when), timing of imitation of tasks and status of progression through the tasks (e.g., to facilitate determining expected time of completion of the tasks), and the like. In some implementations, the resource assessment module 110 can also forecast estimated timing of completion of task that are in-progress (e.g., using one or more machine learning techniques). The resource assessment module 114 can further evaluate scheduling information to determine information regarding amount of time certain workers have available between scheduled task, taking into account locations of the scheduled task, mode of travel between different locations, and expected amounts of time the scheduled task take to complete (e.g., using one or more machine learning techniques). The resource assessment module 114 can also receive and track information regarding location of the respective healthcare workers, movement of the healthcare workers, mobility state in association with traveling from one location to another (e.g., walking, driving, riding as a passenger, etc.). In some embodiments, the resource assessment module 114 can employ one or more machine learning techniques to learn and forecast information regarding availability of certain healthcare workers based on analysis of historical dynamic operating data 104 associated with the specific healthcare workers or similar healthcare workers (e.g., with similar job titles, skill levels, location etc.) under various operating conditions/contexts of the healthcare environment. In some implementations, these machine learning techniques can involve forecasting upcoming demand and expected time in which the healthcare worker will have to perform a healthcare task given the forecasted demand.

Although the embodiments, described above are directed to evaluating and determining availability of healthcare workers (e.g., humans), the resource assessment module 114 can also evaluate relevant dynamic operating data 104 to determine information regarding the availability of other system resources. For example, the other system resources can include supplies, instruments, equipment, machines, technology, and the like that are needed to perform and/or facilitate performance of the healthcare tasks. Thus, in some embodiments, the resources availability data 116 can also include information regarding availability of other resources, such as current availability status of the resources (e.g., whether they are in-use, clean, dirty, in repair, offline, overloaded, power levels, etc.), expected availability status of the resources (e.g., when they will be available for use), locations of the resources, and the like.

Figure 5:
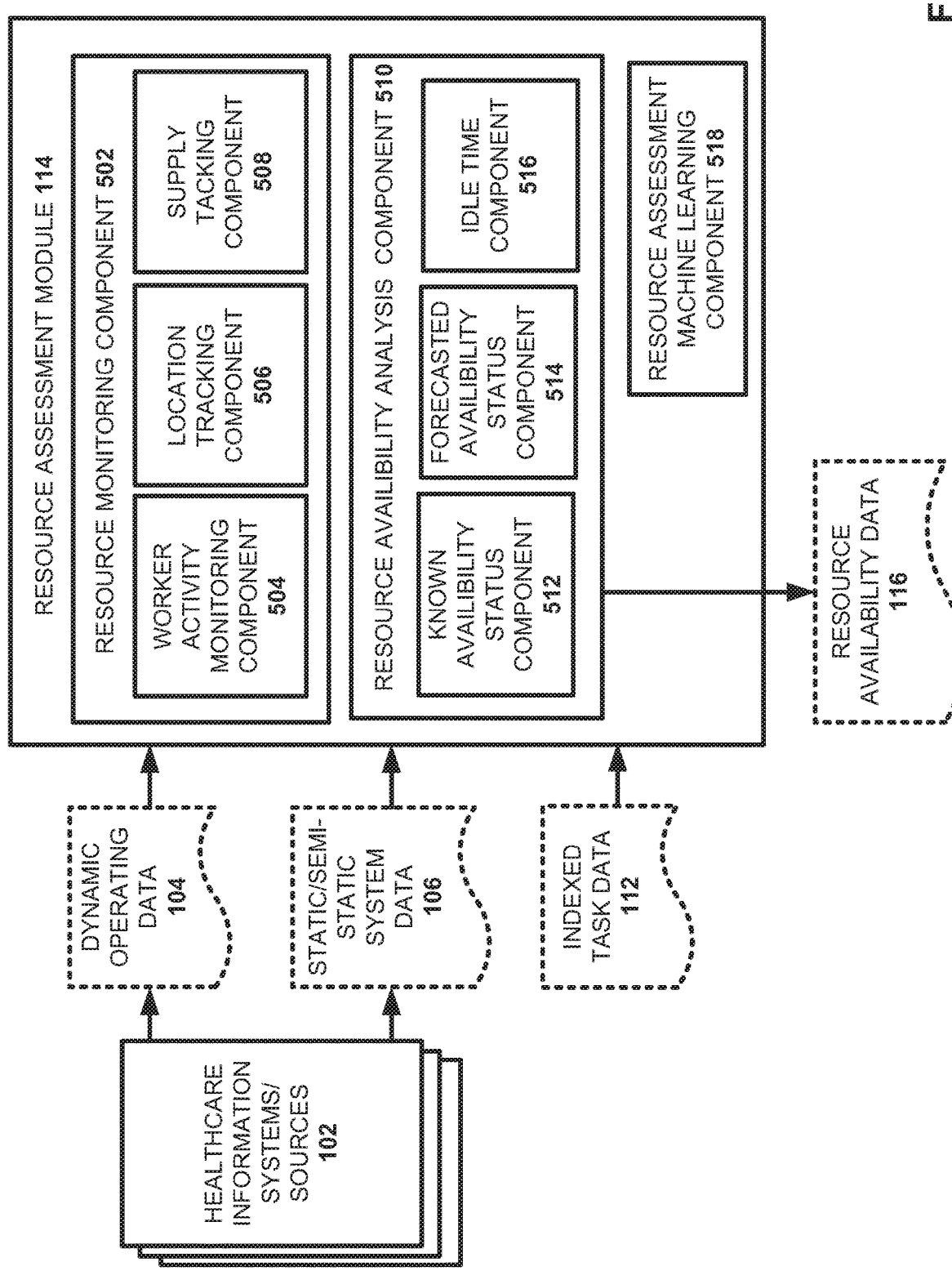
FIG. 5 presents an example resource assessment module that facilitates determining information regarding availability of resources of an integrated healthcare system in accordance with one or more embodiments of the disclosed subject matter.

Additional details regarding the features and functionalities of the resource assessment module 114 are discussed in greater detail infra with reference to FIG. 5.

Turning now to the third component, using parameters provided by the indexed task data 112, the resource availability data 116, the dynamic operating data 104 and the static/semi-static system data 106 as input, the task scheduling and resource assignment optimization module 118 can employ one or more machine learning and/or optimization algorithms/models to determine how to schedule performance of the healthcare tasks to optimize utilization of the available resources in view of patient preference and need. In this regard, the task scheduling and resources assignment optimization module 118 can intelligently determine if a task should performed (e.g., based on authorization restrictions, necessity etc.), when the task should performed, where the task should performed, how the task should be performed (e.g., in person, using telemedicine), who or whom should perform the task (e.g., a person or person), and/or what additional (non-human) resources should be used (e.g., supplies, instruments, equipment, technology, etc.), based one or more optimization criteria. For example, the optimization criteria can include (but is not limited to), facilitating optimal patient flow, minimizing delay between performance of tasks, meeting fixed constraints (e.g., regarding timing and order, location, quality/standard of care, etc.), meeting patient preferences/needs, maximizing utilization of resources, minimizing costs, and/or maximizing revenue.

In association with determining if, when, where, and by whom a pending healthcare task should be performed, the task scheduling and resource assignment optimization module 118 can evaluate the collective state of the entire healthcare environment to determine an optimal scheduling of all (or a grouped subset) of known tasks to be performed (e.g., within a defined, upcoming timeframe). In this regard, the task scheduling and resource assignment module 118 can determine an optimal scheduling (time/location) and resource assignment (specific healthcare workers) arrangement that balances and coordinate constraints, requirements and conditions associated with all tasks with respect to timing, location, and resources to be used for the tasks (e.g., provided by and/or determined by the indexed task data 112), patient needs and preferences (e.g., provided in the static/semi-static system data 106), availability of resources to perform the tasks (e.g., provided by the resource availability data 116), and various attributes associated with the respective resources.

For example, with respect to assigning workers to healthcare tasks, in addition to availability, the task scheduling and resource assignment optimization module 118 can match the "best" worker to the task that maximizes utilization of the available workers based on qualification to perform the tasks, skill level, proficiency level, compensation schedule, worker preference, and the like. Further, as discussed in greater detail infra with reference to FIG. 7, the task scheduling and resource assignment optimization module 118 can employ one or more optimization models that maximize utilization of workers by repurposing uses of the workers in appropriate contexts beyond their primary role and sharing workers across different operating entities based on context and need. With these embodiments, the integrated healthcare system (or individual operating entities) can define all possible types of healthcare tasks each worker can perform based on their qualifications, capabilities, performance level and the like. The healthcare tasks can include healthcare tasks that are traditionally associated with the job title/description, as well as those that are outside of their traditional or primary capacity. For example, the system can identify a set of primary healthcare tasks of a particular surgeon included in the integrated healthcare system, such as the specialized surgery procedures the surgeon is capable of performing. The system can further provide a list of various alternative healthcare tasks the surgeon can perform, including non-surgical tasks, various general clinical tasks traditionally performed by nurses or less specialized clinicians, as well as non-clinical tasks, such as administrative tasks, EVS tasks, and the like. According to these embodiments, the task scheduling and resource assignment optimization module 118 can assign healthcare workers to various types of tasks based on context and need, including tasks that are not their primary role when appropriate to maximize utilization of all workers in every capacity. In some embodiments, the task scheduling and resource assignment optimization module 118 can also factor in expected/forecasted need of certain workers, balancing costs associated with assigning them to a certain task now or waiting to assign them to a more demanding or appropriate task expected to arise in the near future.

In this regard, the task scheduling and resource assignment optimization module 118 can evaluate information for an entire operating environment (e.g., of a single entity or an integrated healthcare system) regarding what needs to be done and when, who is available to do it, and who is the best person/persons to do it, based on a variety of complex and dynamic variables, to determine how to schedule performance of the tasks with respect to time and location and how to assign resources (e.g., workers) to the tasks to ensure the tasks are performed in the most efficient and effective (e.g., in terms of achieve quality of care, in terms of minimizing costs, in terms of maximizing revenue, and the like) manner across all possible options, using the right resources at the right time for the right patient in the right place. From the perspective of the operating entity, or entities in embodiments in which the disclosed techniques are applied to an integrated healthcare system, the optimal scheduling and resource assignment scheme for all (or a grouped subset) of known tasks to be performed (e.g., within a defined, upcoming timeframe) can be selected to balance one or more of the following goals: minimize delays between performance of the healthcare tasks, ensure all healthcare tasks are delivered in accordance with defined quality and regulatory requirements, maximize utilization of available resources, minimize losses, maximize revenue, and meet patient preferences with respect to when, where and who performs healthcare tasks. In embodiments in which the disclosed techniques are applied to an integrated healthcare system involving a plurality of different operating entities, the optimal task scheduling and resource assignment scheme can further balance the goals across the entire system, further considering the many additional constraints associated with coordinating and synchronizing performance of healthcare tasks with interdependencies with respect to order of performance, timing of performance and resources used. The optimal task scheduling and resource assignment scheme for an integrated healthcare system can also consider geographic factors/constraints involving operating entities at various disparate locations, which can further influence where services are scheduled, and timing of scheduling based on travel time, traffic, and the like. In some embodiments, the tasks scheduling and resource assignment optimization module 118 can generate several different scheduling and resource assignment schemes for performing healthcare tasks using different optimization models that are targeted to different goals. For example, one optimization model can be configured to determine a task scheduling and resource assignment scheme that focuses more heavily on minimizing delays between performance of healthcare tasks, while another model can be configured to determine an alternative scheme that focuses more heavily on meeting patient preferences. In this regard, the optimization models can be tailored based on the needs and preferences of the specific operating entity and/or integrated healthcare system that employs system 100 to facilitate optimizing their operations.

The task scheduling and resource assignment optimization modules 118 can further generate task scheduling and resource assignment information 126 that can be regularly updated in real-time regarding the determined optimal scheduling/resource assignment scheme or schemes for an operating entity and/or integrated healthcare system. For example, task scheduling and resource assignment information 126 can identify known healthcare task to be performed at a current point in time and/or over a defined upcoming timeframe, and include information identifying a timing for performance of the respective tasks, a location for performance of the respective tasks, the specific healthcare worker or group of healthcare workers assigned to the task, and in some implementations, specific instruments, supplies, equipment, etc., assigned to the respective tasks. The healthcare tasks can include all known healthcare tasks for integrated healthcare system or subsets of the tasks grouped by a defined grouping criterion, such as by operating entity, by location, by patient, by healthcare worker, by timeframe, etc. The task scheduling and resource assignment information 126 can further be provided to the task management administrators and/or the healthcare workers directly to facilitate performing the healthcare tasks in accordance with the prescribed optimal scheduling and resource assignment scheme. The task scheduling and resource assignment information 126 can also be provided to individual patients to provide a real-time schedule of activities for each patient with anticipated date/time of event and coordinates the sequencing of various activities and services to be rendered (and updated in real-time).

Figure 7:
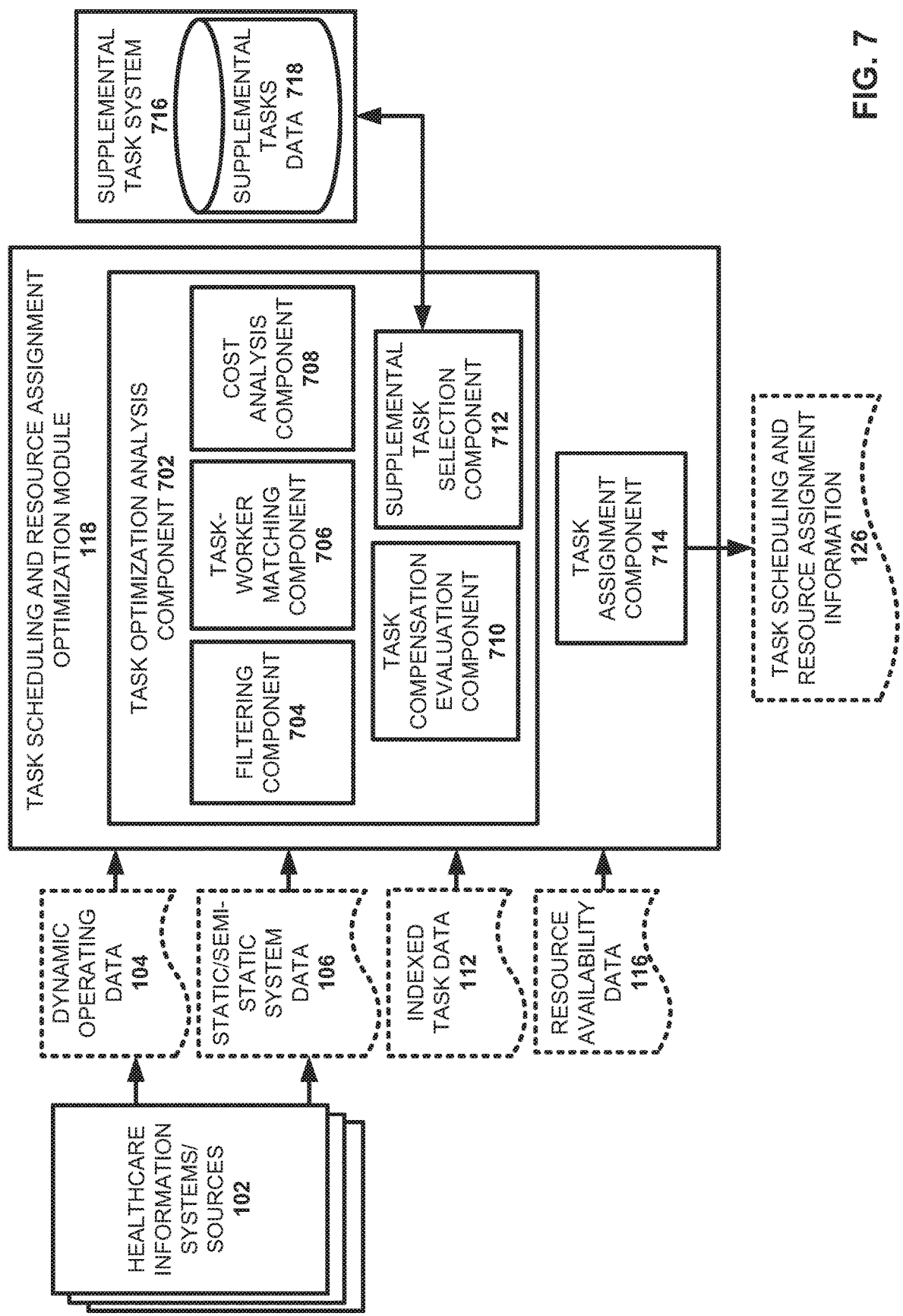
FIG. 7 illustrates an example task scheduling and resource assignment optimization module that facilitates coordinating and optimizing resource utilization and delivery of healthcare services across an integrated healthcare system in accordance with one or more embodiments of the disclosed subject matter.

Additional details regarding the features and functionalities of the task scheduling and resource assignment optimization module 118 are discussed in greater detail infra with reference to FIG. 7.

Figure 2:
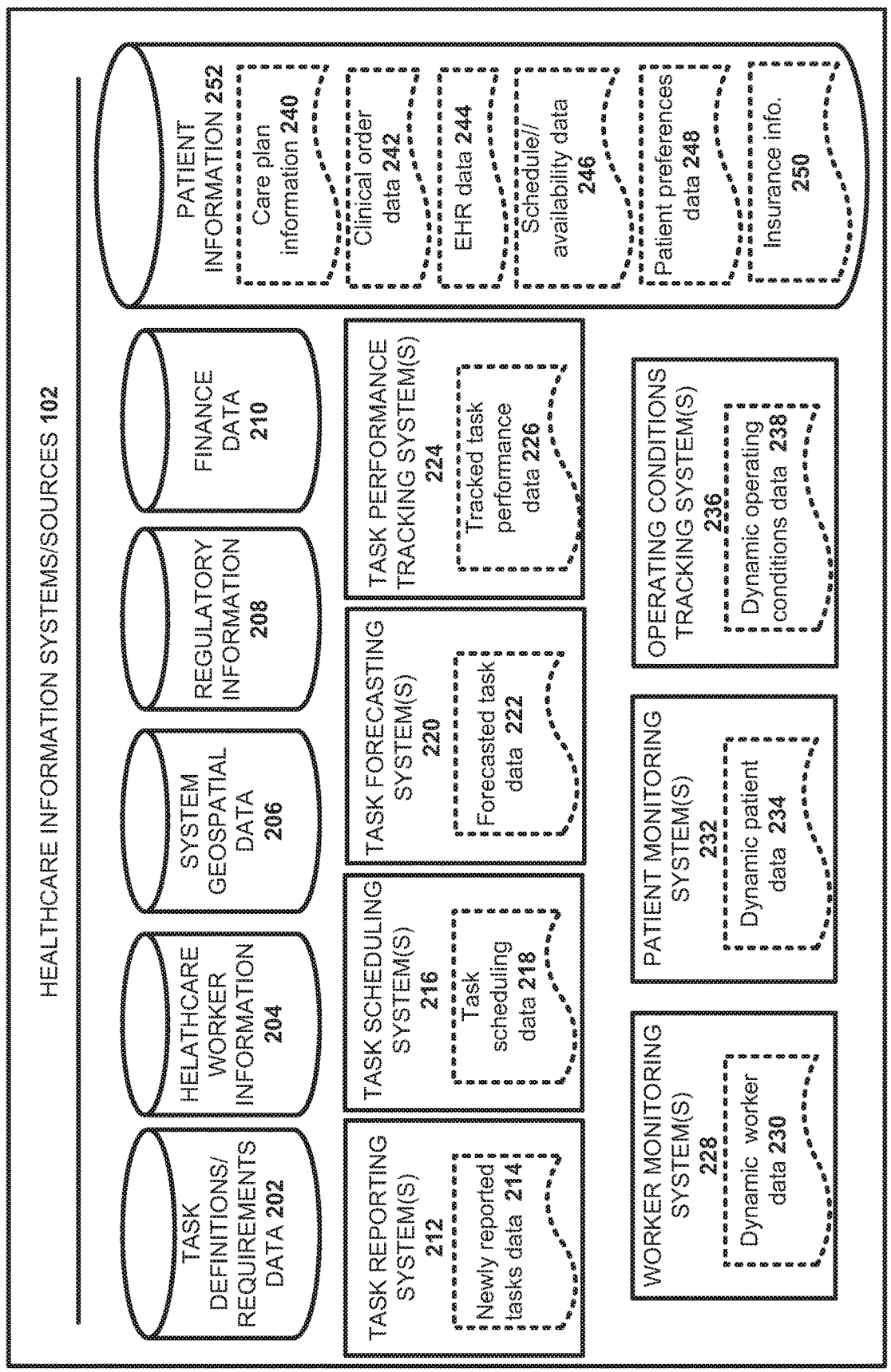
FIG. 2 illustrates example healthcare information systems and sources that can provide information that facilitates coordinating and optimizing resource utilization and delivery of healthcare services across an integrated healthcare system using a machine learning framework, in accordance with one or more embodiments of the disclosed subject matter.

FIG. 2 illustrates example healthcare information systems/sources 102 that can provide information that facilitates coordinating and optimizing resource utilization and delivery of healthcare services across an integrated healthcare system using a machine learning framework, in accordance with one or more embodiments of the disclosed subject matter. The various healthcare information systems/sources shown in FIG. 2 can include databases and systems associated with a single operating entity or a plurality of different operating entities of an integrated healthcare system. The various databases and systems shown in FIG. 2 are merely exemplary and are intended to limit the scope of the various possible data sources and systems that can provide the dynamic operating data 104 and the static/semi-static system data 106. Repetitive description of like elements employed in respective embodiments are omitted for sake of brevity.

In the embodiment shown, the healthcare information systems/sources 102 include one or more databases that provide static/semi-static system data 106 for an operating entity or group of operating entities, including task definitions/requirement data 202, worker information 204, system geospatial data 206, finance data 210 and patient information 252. The task definitions/requirements data 202 can include predefined information that identifies discrete healthcare tasks that are performed by one or more healthcare workers of a healthcare system. The healthcare tasks can include various types of tasks that are performed by a single operating entity and/or that are performed in an integrated healthcare system, including but not limited to, clinical tasks, administrative tasks, EVS tasks, transportation services tasks, food services tasks, technical tasks, ambulatory tasks, and the like. In various embodiments, the task definitions/requirements data 202 can identify defined tasks using a unified or standardized classification system that assigns each discrete task with a unique task identifier that identifies the task and identifies or indicates the requirements of the tasks. For example, in some implementations, known medical procedures can be identified as discrete tasks by standardized procedure codes for the respective medical procedures. Some medical procedures can involve a plurality of associated tasks, such as task that involve preparing the patient, tasks that involves administering medication, task that involve performing surgery, task that involve assisting the surgeon, tasks that involve performing an assessment, tasks that involve operating medical instruments, tasks that involve waste removal, task that involve facilitating patient recovery, and the like. In this regard, a single procedure can be associated with a plurality of discrete tasks, wherein each task can further be defined with a unique that identifies the specific task and indicates requirements of the task.

In some implementations, the unique identifier used for each task can identify or indicate a type of the task such as clinical vs. non-clinical, if clinical a type of the clinical task (e.g., a medical procedure, a medical assessment, an administering of medication, a prescribing of medication), if non clinical, a type of the non-clinical task (e.g., EVS, transportation services, equipment repair, food services, etc.). The task definitions/requirements data 202 can also include information that defines what the task involves, and/or any fixed constraints associated with the respective tasks regarding rules and/or requirements associated with the respective tasks. For example, the definitions/requirements data 202 can include information specifying qualifications and/or credentials of the healthcare workers or workers that are authorized to perform the task. For instance, the qualifications/credentials can list required certifications, levels of experience, performance rating levels and the like. In some implementations, a task can be performed by a wide range of healthcare workers with different types of qualifications, such as a licensed paramedic, a midwife, a nurse, a nurse practitioner, a physician's assistant, a general physician, and a specialized physician. With these implementations, the qualifications/credentials information can include system preference information that ranks the different types of credentials/qualifications accepted based on preference for performing the task, wherein workers with a certain credentials are considered more preferred than workers with other credentials (e.g., this task is most preferably performed by a nurse, second most preferably performed by a nurse practitioner, and third most preferably performed by a physician). The healthcare worker requirements information can also identify a number of healthcare workers required and/or preferred for performing certain tasks.

The rules/requirements associated with a task can also include information identifying or indicating a relative priority level of a task (e.g., in accordance with a defined priority level coding/ranking scheme), as well as information identifying or indicating any performance dependency constraints with other tasks. For example, performance dependency constraints can identify or indicate an order for performing a task relative to another related task. Performance dependency constraints can also identify or indicate task groupings including tasks that must be performed together and/or by a same healthcare worker or healthcare workers. Other example rules/requirements information that can be associated with defined tasks can include rules/requirements regarding non-manual supplies to be used in association with performing the tasks, such as required medical supplies, instruments, equipment, etc.

The healthcare worker information 204 can include known information about the different healthcare workers employed by and/or affiliated with (e.g., as volunteers, independent contractors, as personal patient aids/friends/family, etc.) an operating entity or group of operating entities of an integrated healthcare system. In this regard, the healthcare worker information 204 can include information identifying the respective healthcare workers (e.g., by name or another unique identifier) and their job title or role. The healthcare worker information 204 can further include (but is not limited to), information identifying the primary operating entities or entities where the healthcare worker works, the location of the operating entity or entities (including a geographic area where the worker travels for work), and their employment history with the operating entity or entities. The healthcare worker information 204 can also include (but is not limited to), compensation information identifying the compensation schedule/salary of the workers, their demographic information (e.g., gender, age, ethnicity, etc.), home address/location, their contact information (e.g., phone number, email address, social medial connections, etc.) and the like.

In various embodiments, the healthcare worker information 204 can further include task capability information that identifies (e.g., by task identifier) or indicates discrete healthcare tasks (or groups of tasks) the healthcare worker is capable of and/or qualified to perform. With these embodiments, various healthcare workers can be capable of performing and/or qualified to perform a variety of different healthcare tasks in the healthcare system. These different healthcare tasks can include those that traditionally fall under their job title and/or that are their primary tasks in the system given their defined role in the system, as well as various alternative or secondary healthcare tasks that may not be traditionally performed by their job title/description. In this regard, the healthcare worker information 204 can provide a list of all possible healthcare tasks that are performed (or that may arise) in the healthcare system that the healthcare worker is capable and qualified to perform, enabling the system the ability to utilize each worker in the best capacity depending on the contextual needs of the system and the contextual availability of workers capable of performing the types of tasks that are needed for performance at any given time.

In some implementations of these embodiments, the healthcare worker information 204 can further include preference information for the respective tasks each worker is capable/qualified to performed regarding a preference of performance of the respective tasks. For example, the preference information can include system defined preference information for each task/worker combination that reflects the healthcare system or operating entity's preference for utilization the healthcare worker for the specific task relative to other tasks the healthcare worker is capable/qualified to perform. For instance, assume a surgeon is capable of performing a highly complex procedure as well as various general clinical tasks. With this example, the system can prefer the surgeon perform the highly complex procedure over the general clinical tasks, as this would in most scenarios be the most useful application of the surgeon's skills. Thus, the system can associate a higher preference rating with the complex procedure relative to the general clinical tasks. The preference information can also include worker preference rating information that provides a worker defined preference rating for performing different task reflective of the workers' personal preferences for performing certain tasks over others that the worker is capable/qualified to perform.

The task capability information can further include information associated with the respective tasks that a worker is capable/qualified to perform regarding historically tracked and/or scored performance metrics for the respective tasks. For example, the performance metrics can include a general performance rating provided by the healthcare system that reflects the performance quality (e.g., measured by system review, employee feedback, patient feedback, etc.), efficiency, and proficiency of the healthcare worker in association with performance of each task. The performance metrics can also include information regarding the number and/or frequency of performance of the respective tasks. The performance metrics can also include information regarding historical error/complication rate. The task capability information can also include information regarding compensation schemes for compensating the healthcare worker for performing the different tasks. For example, in some implementations, a healthcare worker can be paid the same rate regardless of the specific task that the worker performs. In other embodiments, the healthcare worker can be paid different rates depending on the type of task and/or the specific task.

The system geospatial data 206 can include mapping information regarding the relative physical locations of fixed structures and objects of a healthcare environment. For example, the geospatial data 206 can include mapping information for a single medical facility, including information identifying the physical address of the medical facility, as well as mapping information identifying the physical layout of the facility, including the layout and locations of different floors, medical units, rooms, hallways, doors, etc. In implementations in which the healthcare environment includes an integrated healthcare system with a plurality of different operating entities provided at various different physical locations (e.g., within a same city, state, region, country etc.), the system geospatial data 206 can also include mapping information for each individual operating entity.

The regulatory information 208 can include defined rules or regulations that provide guidelines regarding how to perform specific task and/or procedures circumstances. These rules or regulations are generally referred to as standard operating procedures (SOPs). For example, emergency room physicians have SOPs for patients who are brought in an unconscious state; nurses in an operating theater have SOPs for the forceps and swabs that they hand over to the operating surgeons; and laboratory technicians have SOPs for handling, testing, and subsequently discarding body fluids obtained from patients. Medical procedures can also be associated with SOPs that provide guidelines that define how to perform the procedure (e.g., steps to perform and how to perform them), how to respond to different patient conditions in association with performance of the procedure, how to respond to complications that arise, and other type of events that may arise over the course of the procedure, and the like. Some healthcare organizations can also establish or adopt SOPs for medical conditions that can define standard medical practices for treating patient's having the medical condition and the respective medical conditions. Some healthcare organizations can also have SOPs regarding providing healthcare to patients having two or more medical conditions (e.g., referred to as comorbidity). In this regard, the regulatory information 208 can include information that identifies and/or defines one or more standardized or defined protocols for following in association with performance of a procedure, treating a patient with a condition, and/or responding to a clinical scenario. For example, with respect to a procedure, the workflow information can identify procedural steps or processes to be performed and when, timing of the steps, information regarding how each step/process should be performed, and the like The finance data 210 can include any type of financial information pertaining to costs associated healthcare task and services. For example, the finance data 210 can include costs associated with different procedures and utilization of different resources, including human resources as well as medical instruments and supplies. In some implementations, the finance data 212 can include historical costs, such as historical costs associated with past procedures, courses of care and the like. For example, with respect to past procedures, the finance data 210 can identify total costs (e.g., to the healthcare organization) of each procedure performed, as well as line item costs associated with individual components of the procedures, including supplies/equipment costs, personnel costs, room/space costs, individual process or procedural steps, and the like. In some implementations, finance data 210 can also include information regarding reimbursement for respective procedures, including total reimbursement and reimbursement for procedural components. In some implementations, the finance data 210 can also include cost information attributed to LOS, procedure complications, and procedural and/or clinical errors (e.g., including cost attributed to litigation associated with the error).

The patient information 252 can include patient information regarding current patients of one or more healthcare systems (e.g., patients that have entered the healthcare system via at least one entry point) and their medical needs. For example, the patient information 252 can include care plan information 240 that describes or defines care plans for the patients (if available). For example, the care plan can include information a list or timeline of the various prescribed clinical treatment to for the patient in association with a course of patient care. In some implementations, the care plan information can also be associated with information identifying patient rest and recovery periods/times, such as amounts of time and/or periods of time during which the patient is required or preferred to rest (e.g., between procedures or appointments and the like). In some implementations, the care plan information can be automatically generated and provided by an artificial intelligence (AI) system configured to evaluate a patient's condition, diagnosis, needs and medical history and generate a care plan accordingly. In some implementations, the AI system can also evaluate information regarding the patient's insurance plan/carrier and/or form of payment in association with determining the type of services that are available to the patient for including in the patient's care plan (e.g., only those services that are approved or anticipated for approval by the patient's insurance provider). The patient information 252 can also include clinical order data 242 providing clinical order prescribed for a patient. The patient information can also include medical history information for current and past patients, such as that provided in the EHR data 244. For example, the patient medical history information can include internal information for patients associated with a single healthcare organization as well as information aggregated for patients across various disparate healthcare organizations/vendors (e.g., internal and third-party organizations/vendors) via a healthcare information exchange system (HIE). The patient information 252 can also include patient preferences data 248 that describes any patient preferences regarding where, when, how and by whom the would prefer to receive various medical services (e.g., preferred locations, preferred scheduling times, preferred rest times/amounts, preferred characteristics of the healthcare workers, etc.). The patient information 252 can also include insurance information 250 for the patients that can control if a patient can receive certain services, where they can receive them, costs of services, and the like.

The healthcare information systems/sources 102 include also one or more systems that provide dynamic operating data 104 for an operating entity or group of operating entities (e.g., of an integrated healthcare system), including one or more task reporting systems 212, one or more task scheduling systems 216, one or more task forecasting systems 220, one or more task performance tracking systems 224, one or more worker monitoring systems 228, one or more patient monitoring systems 232, and one or more operating conditions tracking systems 236.

The one or more task reporting systems 212 can include various systems that facilitate reporting known healthcare tasks that need to be completed at a healthcare system. For example, the one or more task reporting systems 212 can include data entry systems associated various healthcare operating entities, units, departments, etc., that receive user input reporting new tasks that have be generated in the system. For instance, the new tasks can be reported via text, via audio feedback, by electronic clinical ordering systems, and the like. These task reporting systems 212 can provide newly reported task data 214 regarding the tasks. For example, the newly reported task data 214 can identify the task and include any user/system provided attributes associated with the tasks (e.g., regarding the patient associated with the task, timing constraints associated with the task, location constraints associated with the task, etc.). In some implementations, the task reporting systems 212 can include patient request systems that receive patient initiated request for medical services which can be treated as newly reported tasks. In other implementations, the task reporting systems 212 can include one or more automated systems configured to automatically determine and generate new tasks to be performed based on new data points included in the dynamic operating data 104. For example, the task reporting systems can include an AI system that determines new tasks to be performed based on information regarding results/outputs of previously completed tasks, monitored changes in patient conditions/status, monitored changes in healthcare worker task performance, and the like. For instance, the AI system can evaluate newly received laboratory data for a patient to determine a new task that needs to be performed in response to the specific values reflected in the laboratory data.

The one or more task scheduling systems 216 can include electronic scheduling systems for one or more operating entities that are used to schedule task, such as patient appointments, patient procedures and the like. In this regard, the task scheduling systems 216 an provide task scheduling data 218 regarding tasks scheduled for performance at specific times, places and/or locations and with specific clinicians. The task scheduling data 216 can also provide scheduling information for healthcare workers regarding their scheduled tasks and appointments and scheduling information for patients regarding their scheduled appointments.

The task forecasting systems 220 can include various machine learning systems configured to generate forecasted data 222 for a healthcare system regarding forecasted tasks expected to arise over a defined, upcoming timeframe. For example, the forecasted task data 222 can identify general demand information regarding expected demand for all tasks, as well as more precise information regarding expected tasks of a specific type, for a specific patient (e.g., patient John Andrews is expected to need a re-op procedure tomorrow around 3:00 pm), a specific time or time frame expected for the task, the expected duration of the task, expected location of the task, and the like.

The one or more task performance tracking systems 224 can include various electronic tracking systems that monitor and/or generate tracked task performance data 226 regarding progress of performance of reported and/or scheduled tasks, including information regarding who performs them, where they are performed and performance quality. For example, the one or more task performance tracking systems 224 can include a task tracking system that receives user feedback provided the respective healthcare workers reporting what they are doing, including information reporting when they initiate a task and when they complete the task. In some implementations, the task tracking system can also determine and/or provide information tracking the progress of the task to completion (e.g., based on an expected duration of the task and/or based on tracking performance of known actions/steps associated with the task). In some implementations, the task tracking system can also allow workers to provide same or similar feedback for other workers. Feedback signals capturing information about the activity of the workers using various sensors, including (but not limited to) motion sensors, biofeedback sensors, images, imaging sensors (e.g., live/video, still images) and/or audio sensors. For example, in some implementations, the sensory feedback can be provided by one or more worker monitoring systems 228. The task performance tracking system 224 can further determine what the workers are doing based on the sensory feedback, including whether they are performing a task, what task they are performing and the like. In some embodiments, the task performance tracking system can evaluate this sensory in conjunction with the user provided feedback to facilitate determining what the workers are doing, including determining when the worker reported activity contradicts with the sensory feedback and vice versa. This sensory feedback can also facilitate determining when a worker has idle time, including idle time between tasks and/or during tasks.

The one or more worker monitoring systems(s) 228 can include one or more systems associated with a healthcare system (e.g., including a single operating entity or group of operating entities (of an integrated healthcare system)) that track and provide dynamic worker data 230 regarding the dynamic activity of healthcare workers of the healthcare system over the course of operation of the healthcare system. For example, one or more worker monitoring systems 228 can include various sensory tracking systems that monitor and receive feedback signals capturing information about the activity of the workers using various sensors, including (but not limited to) motion sensors, biofeedback sensors, images, imaging sensors (e.g., live/video, still images) and/ or audio sensors. In some implementations, the one or more worker monitoring systems 228 can further determine what the workers are doing based on the sensory feedback, including whether they are performing a task, what task they are performing and the like. The one or more worker monitoring systems can also include location and/or motion tracking systems configured to track real-time information regarding current location of the healthcare workers, live movement data regarding movement of the healthcare workers from one location to another, mobility data regarding mode of transportation/movement (e.g., driving, walking, riding as a passenger, etc.), motion data regarding precise body motions of the workers, and the like.

The one or more patient monitoring systems 232 can include various systems configured to track and monitor dynamic patient data 234 information regarding the location and physiological state of patients. For example, the patient monitoring systems can 232 track location and movement data regarding the real-time location and movement of the patients. The patient monitoring systems 232 can also include systems that monitor and receive real-time physiological data for patients regarding their current physiological state from one or more biofeedback devices and/or audio/visual monitoring devices. For example, the dynamic patient data 234 can include real-time data regarding monitored physiological parameters of the patient, movement of the patient, appearance of the patient, and the like, that can be used to determine if clinical care is necessitated and if so, what healthcare tasks are involved (e.g., administering medication, performing a medical procedure, helping the patient out of bed, etc.). In another example, the task identification component 304 can evaluate dynamic operating conditions data 238 regarding current states of medical instruments, supplies, equipment, etc., to determine needed healthcare tasks involving the cleaning, restocking, and/or repairing of the medical instruments, supplies, and/or equipment The one or more operating conditions tracking system(s) 236 can include one or more systems associated with a healthcare system (e.g., including a single operating entity or group of operating entities (of an integrated healthcare system)) that track and provide dynamic information regarding the current operating conditions of the healthcare system. For example, can include a variety of parameters regarding the operations conditions, context and or state of the dynamic system at a given point in time that can impact (e.g., either directly or indirectly) if, when, and where tasks are scheduled and who or whom is assigned to the tasks. The dynamic operating conditions data 238 will also thus vary based on the type of dynamic system evaluated. For example, in implementations in which the dynamic system is a hospital, the dynamic operating conditions data 238 can include but is not limited to: current occupancy levels of the hospital, status of beds at the hospital (e.g., occupied, assigned, clean, dirty, etc.), number of patient waiting for beds, predicted wait times for occupied beds (e.g., determined based on level/type of care needed, recovery time, procedures scheduled, etc.), estimates of census pressure on source units where patients are waiting for beds, locations of the beds (e.g., by medical unit), and types of the beds. The dynamic operating conditions data 1238 can also include information regarding supplies/equipment used in association with performance of the tasks, such as supply/equipment availability (e.g., available, in-use, out-of-stock,), status (e.g., clean/dirty, etc.), supply/equipment location, and the like. The dynamic operating condition data 238 can also include various additional types of information about the healthcare environment, such as contextual information regarding time of day, day of week/year, weather, localized events or conditions at the hospital (e.g., emergency or crisis scenarios, disease outbreaks), local events associated high influx of patients, etc.), location and status of ambulatory services and the like.

FIG. 3 presents an example task assessment module 108 that facilitates determining information regarding currently pending and forecasted healthcare tasks for performance by one or more operating entities of an integrated healthcare system in accordance with one or more embodiments of the disclosed subject matter. In various embodiments, the task assessment module 108 can include task information extraction component 302, task identification component 304, task grouping component 308, task ordering component 310, attribute defining component 312, task status monitoring component 314, and task indexing component 316 and task assessment machine learning component 318. Repetitive description of like elements employed in respective embodiments is omitted for sake of brevity.

The task assessment module 108 can provide for extracting, evaluating and indexing task information regarding the various healthcare tasks to be performed at a healthcare system over a defined, upcoming timeframe. The various healthcare tasks can include known tasks that are scheduled for performance over the defined, upcoming timeframe or otherwise tasks for which there is existing knowledge that the task exists and needs to be (or should be) completed over the upcoming timeframe. These tasks are collectively referred to herein as "currently pending" tasks. In some embodiments, the various healthcare tasks can also include forecasted healthcare tasks, which can include tasks that are expected to arise over the defined, upcoming timeframe.

The defined, upcoming time can include a timeframe from a current point in time to a specified time in the future, such as the next hour, the next 6 hours, the next 24 hours, the next 48 hours, the current workday (e.g., till closing time), the next workweek, the next month etc. The defined timeframe can vary. For example, with respect to a hospital that runs 24 hours a day, the relevant defined timeframe can include an hourly timeframe or a 24-hour timeframe. On the other hand, with respect to specialty healthcare provider's physical office that sees patient's in accordance with a standard workweek schedule (e.g., 9:00 am to 5:00 pm, Monday through Friday), the relevant timeframe can include a workday, work week, or work month timeframe. In this regard, depending on the type of operating entity and timeframe evaluated, the task information can reflect healthcare tasks that need to be performed immediately, healthcare tasks that need to be performed over the next hour, healthcare tasks that need to be performed over the current workday, healthcare tasks that need to be performed over the current workweek, healthcare tasks that need to be performed over the next month, two months, etc. Also, depending on the type of operating entity and timeframe evaluated, the healthcare tasks can include tasks scheduled for performance as specific points in time (e.g., patient appointments scheduled for specific dates and times), healthcare tasks scheduled and/or requested for performance over a relatively recent timeframe or window of time (e.g., the next hour, the next 24 hours, between 2:00 pm and 5:00 pm, etc.), healthcare tasks that need to be preformed as soon as possible (e.g., urgent/critical tasks), and the like.

Accordingly, in embodiments in which the disclosed techniques are applied to an integrated healthcare system that includes a plurality of different operating entities with different operating environments (e.g., hospitals, specialized hospital units, specialized physician clinics/offices, outpatient facilities, ambulatory services, nursing home facilities, surgery centers, imaging/diagnostic providers, pharmacy providers, traveling/in-home patient care, rehabilitation providers, telemedicine providers, etc.), the task information extracted and evaluated for all the different operating entities combined can reflect various different types of tasks for performance over various different timeframes with various different time constraints associated with the respective tasks. Further, in some embodiments, the task information can include tasks to be completed over different timeframes for a same operating entity or group of operating entities (e.g., one timeframe can identify all tasks that need to be completed over the next hour, another timeframe can identify all tasks that need to be completed of the next 12 hours, another timeframe can identify all tasks that need to be completed of the next 24 hours, and the like).

The task assessment module 108 can include task information extraction component 302 to extract (or otherwise receive) the task information from the one or more healthcare information system/sources 102 regarding the various healthcare tasks to be performed at a healthcare system over a defined, upcoming timeframe. For example, with reference again to FIG. 2, the task assessment module 108 can extract and/or receive the task information from the one or more task reporting systems 212 (e.g., the newly reported tasks data 214), the one or more tasks scheduling systems 216 (e.g., task scheduling data 218), and/or the one or more task forecasting systems 220 (e.g., the forecasted task data 222). The task information extraction component 302 can further regularly or continuously extract and/or receive the task information over a course of operation of the healthcare system to account for new tasks that arise over the course of operation, enabling a real-time understanding of all the tasks to be performed over the defined, upcoming timeframe.

The task identification component 304 can further process the extracted/received task information (e.g., the newly reported tasks data 214, the task scheduling data 218, and/or the forecasted task data 222) to identify all (or defined subsets) of the discrete tasks reflected in the task information for performance over the defined, upcoming timeframe. For example, the task identification component 304 can evaluate the extracted/received task information in view of the task definitions/requirement data 202 providing task identifiers and associated definitions for defined discrete healthcare tasks to identify the defined discrete healthcare tasks included in the extracted/received task information.

In some embodiments, the task identification component 304 can also evaluate patient information regarding current patients of a healthcare system (e.g., patients that have entered the healthcare system via at least one entry point) and their medical needs to determine discrete tasks associated with each patient to be completed by healthcare workers of the healthcare system over the defined, upcoming timeframe to satisfy the medical needs of the current patients over the defined, upcoming timeframe. For example, in the embodiment shown, the task identification component 204 can include care plan breakdown component 306 to evaluate care plan information 240 for a patient and identify discrete healthcare tasks to be performed for the patient based on the various clinical actions and activities described/defined in the care pan information 240. In this regard, the care plan breakdown component 306 can evaluate care plan information 240 for the current patients to identify the various discrete healthcare tasks to be performed for the patient over a course of care and/or within the defined upcoming timeframe, such as discrete procedures to be performed, medications to be administered, assessments to be made, and the like. In some embodiments, the care plan breakdown component 306 can also access and evaluate clinical order data 242 for a patient to identify discrete healthcare tasks for performance for the patient of the defined, upcoming timeframe.

In some embodiments, in association with identifying discrete healthcare tasks, the task identification component 304 can be configured to identify discrete healthcare tasks that can be fulfilled by a single healthcare worker or group of healthcare workers. This enables discrete healthcare tasks associated with a single patient (or grouped together by another aggregation factor) to be distributed to different healthcare workers (or groups of healthcare workers). For example, some healthcare operating models often assign healthcare workers to a specific patient for the course of the patient's care or another defined timeframe. Under these models, the healthcare worker is generally responsible for performing all the healthcare tasks associated with that patient. However, in various contexts, another healthcare worker may be more appropriate for performing one or more of healthcare tasks for the patient. For example, an alternative healthcare worker may be more appropriate for performing a particular task associated with the patient based on the availability of the original healthcare worker and the alternative healthcare worker, the location of the healthcare worker and the location of the patient, the expertise of the healthcare worker in association with performing the particular task, the demand for the original healthcare worker in another capacity, and the like. Thus, in some embodiments, the task identification component 304 and/or the care path breakdown component 306 can be configured to segment tasks associated with a single patient into a plurality of discrete tasks that can be distributed to different healthcare workers. The task identification component 304 can similarly segment tasks generally grouped for a performance by a single healthcare worker (e.g., task located in a particular location, tasks of a specific type, etc.) into separate tasks that can be assigned to different healthcare workers.

In some embodiments, the task identification component 304 can also access (or receive via the task information extraction component 302) and evaluate dynamic patient data 234 (e.g., provided by one or more patient monitoring systems 232) and/or dynamic operating conditions data 238 (e.g., provided by one or more operating conditions tracking systems 236) to identify discrete healthcare tasks for performance over a defined, upcoming timeframe. With these embodiments, the task identification component 304 can evaluate the data to uncover discrete healthcare tasks that are needed for performance when the data itself does not explicitly call out the discrete healthcare tasks are needed. In this regard, the task identification component 304 can examine dynamic information the current context and state of the patients and the current operating context of the healthcare environment to determine what needs to be done, when and where, to account for the patient's needs. For example, the task identification component 304 can evaluate dynamic patient data 234 in real-time regarding monitored physiological parameters of the patient, movement of the patient, appearance of the patient, and the like, to determine if clinical care is necessitated and if so, what healthcare tasks are involved (e.g., administering medication, performing a medical procedure, helping the patient out of bed, etc.). For instance, the task identification component 304 can determine, based on monitored physiological data for a patient, that emergency services are needed for dispatch to the patient and generate task information that identifies the one or more discrete tasks involved with provision of the emergency services to the patient. In another example, the task identification component 304 can evaluate dynamic operating conditions data 238 regarding current states of medical instruments, supplies, equipment, etc., to determine needed healthcare tasks involving the cleaning, restocking, and/or repairing of the medical instruments, supplies, and/or equipment.

As noted above, in various embodiments, the task identification component 304 can identify all tasks for performance over a defined upcoming timeframe, including currently pending tasks and in some implementations, forecasted tasks. These tasks can be grouped by operating entity, location, timeframe (e.g., within the next hour, the next 24 hours, the next month, etc.), by type, by patient, by priority level, or another suitable attribute. In one or more embodiments, the task grouping component 308 can perform or facilitate such grouping of tasks. The task grouping component 308 can also provide for grouping tasks for performance by a single healthcare worker or groups of healthcare workers. For example, in various embodiments, the task identification component 304 can specifically identify discrete tasks that can be performed by a single healthcare worker or group of healthcare workers. In other embodiments, certain discrete tasks identified by the task identification component 304 can include groups of two or more tasks that should be and/or are preferred for performance by a same healthcare worker or group of healthcare workers (e.g., as defined in the task definitions/requirement data 202, as provided in the regulatory information 208, and/or as determined using machine learning techniques). With these embodiments, the grouping component 308 can also provide for identifying two or more tasks that should be (or are recommended to be) performed by a same healthcare worker or group of healthcare workers.

For example, in some embodiments, the task definitions/requirement data 202 can identify specific tasks (e.g., by their task identifiers) that should be (or are preferred to be) performed by a same healthcare worker or group of healthcare workers based on the task definitions/requirement data 202 and/or the regulatory information 208. In other embodiments, the task grouping component 308 can employ various machine learning techniques (e.g., provided by the task assessment machine learning component 318) to learn groups of tasks that are best performed by a same healthcare worker or group of healthcare workers, based on analysis of historical data gathered from the healthcare information systems/sources 102. This can include for example, two or more tasks that when performed by a same healthcare worker or group of healthcare workers, (as opposed to different healthcare workers of teams), results in less overall time to complete the tasks, better clinical results, higher quality of care, greater patient satisfaction, fewer complications, fewer costs, and the like. For example, two or more task that may be grouped for performance by a same healthcare worker or group of healthcare workers can include tasks associated with a same procedure, two or more related tasks for performance at a same location, for a same patient and/or over relatively short timeframe, and the like.

The task ordering component 310 can also determine dependencies between tasks that influence ordering of the healthcare tasks relative to one another. For example, certain healthcare tasks associated with a medical procedure, course of patient care, and the like, must be performed in a synchronous manner, while others can be performed asynchronously. In this regard, the task ordering component 310 can determine ordering information for two or more related tasks regarding a required or preferred order for performing the two or more related tasks. With reference to FIG. 2, in some implementations, information defining a required or preferred order for performing two or more related tasks can be provided in and/or determined by the task definitions/requirements data 202, the regulatory information 208, the newly reported tasks data 214 (e.g., based on user input in association with reporting the tasks using a task reporting system of the one or more task reporting systems 212), the care plan information 240, and/or the clinical order data 242. With these implementations, the task ordering component 310 can determine ordering constraints for two or more tasks using these data sources or similar data sources. In other embodiments, the task ordering component 310 can employ various machine learning techniques to learn ordering constraints for two or more healthcare tasks (e.g., provided by the task assessment machine learning component 318) based on analysis of historical performance data gathered from the healthcare information systems/sources 102. This can include for example, a specific manner for ordering performance of two or more tasks that results in less overall time to complete the tasks, better clinical results, higher quality of care, greater patient satisfaction, fewer complications, fewer costs, and the like.

The attribute defining component 312 can be configured to determine and/or associate attribute information (e.g., metadata) with each (or in some implementations one or more) of the discrete healthcare tasks identified by the task identification component 304 based on the dynamic operating data 104 and/or the static/semi-static system data 106 provided the one or more healthcare information systems/sources 102. The attribute information can include various parameters/attributes associated with the respective healthcare tasks regarding constraints, conditions and/or requirements of the healthcare tasks that can influence if the task is performed (e.g., based on authorization restrictions, necessity etc.), when the task is performed, where the task is performed, how the task is performed (e.g., in person, using telemedicine), who or whom performs the task (e.g., a person or person), and/or what additional (non-human) resources are used (e.g., supplies, instruments, equipment, technology, etc.). For example, for each identified healthcare task (e.g., currently pending and/or forecasted), the attribute defining component 312 can associate a task identifier with the healthcare task that uniquely identifies the task. With reference again to FIG. 2, in some embodiments, the attribute defining component 312 can further access the task definitions/requirements data 202 to determine and associate attribute information with the respective tasks identifying the fixed constraints associated with the respective tasks defined therein. In other embodiments, downstream components can look up the various fixed requirements associated with an identified task in the task definitions/requirements data 202 using the task identifier for the task.

The attribute defining component 312 can further determine (e.g., using the dynamic operating data 104 and/or the static/semi-static system data 106 provided by the one or more healthcare information systems/sources 102) and/or associate other attribute information with the identified tasks, including but not limited to: location attribute information regarding one or more locations associated with the task, time attribute information regarding timing associated with performance of the task, patient attribute information regarding one or more patients associated with the task, priority attribute information regarding a priority of the task, grouping/ordering attribute information regarding one or more grouping and/or ordering constraints associated with the task, and the like.

The location attribute information can include location related attributes identifying or indicating one or more locations where the task is required to be performed or can be performed. For example, in implementations in which the healthcare system includes a plurality of different operating entities, the location related attributes can identify the specific operating entity/provider responsible for performing the task and/or where the task otherwise originated. The location related attributes can also identify or indicate a physical location of the operating entity if the operating entity has is associated with a fixed physical location or area (e.g., determined using the system geospatial data 206). In other implementations in which the operating entity has several locations, such as several locations within a same geographical area (e.g., a city, a state, etc.), a same complex (e.g., different buildings associated with a same complex), a same building (e.g., different medical units or areas within a hospital), etc., the location related attributes can identify the specific location (e.g., the specific building, medical unit, etc.), where the task is required to be performed and/or can be performed. In various implementations in which there are several optional locations for performing a task, the location attributes can identify the different options. In addition, the location attributes can identify whether a location for performing the task is fixed (e.g., cannot be changed, based on regulatory requirements, system requirements, task constraints, a priority or urgency level associated with the task, patient preferences/needs, etc.) or flexible.

In some implementations, a healthcare task can involve a plurality of locations, such as a task that involving the transportation of a patient and/or supplies, tools, equipment, etc. With these implementations, the location attribute information can identify the different locations involved, including start and end locations. In other implementations, a healthcare task can involve a location external to an operating entity, such as offsite locations where patients are located (e.g., accident sites, home locations, etc.) where the task involves traveling to the patient. With these implementations, the location attributes can identify the location of the patient and/or whether the patient needs transportation to a destination location (e.g., an emergency room of a local hospital). For example, the patient location can be reported in the newly reported task data 124, in the task scheduling data 218 and/or the dynamic patient data 234. Still in other implementations in which a task involves a non-admitted patient, such as a task involving scheduling a patient appointment for a procedure with a specialist, scheduling the patient for an assessment, scheduling the patient for a medical imaging study, etc., the location attributes can identify a home location, a preferred location and/or geographic area of the patient that is a suitable or preferred location for scheduling the appointment (e.g., determined using the EHR data 244 and/or the patient preferences data 248). The location attributes can also include patient preferences for locations at which the patient prefers to receive medical services, including specific locations for specific types of medical services (e.g., determined using the patient preferences data 248). Still in other implementations, a healthcare task can include a telemedicine task wherein the location of the task can be anywhere a healthcare worker can perform the telemedicine task using a suitable electronic communication device.

The time attribute information can include (but is not limited to) attributes identifying or indicating: a time of origination of a healthcare task, a specific time or timeframe for completing the task (e.g., asap, once every 3 hours, by the end of the day, before 3:00 pm, between noon and 8:00 pm, between April $16^{th}$ and May $10^{th}$, etc.), and expected duration of the task or time to complete the task. In some implementations, the timing attribute information associated with a task can be based on patient preference information associated with certain tasks indicating preferred or required timing for performance of the tasks (e.g., provided in the patient preferences data 248, provided with patient-initiated requests for clinical services included in the newly reported tasks data 214, etc.). The timing attribute information associated with a task can also include information regarding preferred or required patient rest periods when certain tasks should not be performed. In some implementations, the timing attributes can include information indicating whether the time constraint associated with the task is fixed of flexible. For example, a low priority task scheduled for completion by the end of the day may be classified as flexible, indicating that it can be pushed to the next day without resulting in significant complications or losses. On the other hand, a scheduled appointment for a high priority procedure at specific point in time may be classified as fixed, indicating that the procedure cannot be rescheduled or moved.

The patient attribute information can identify one or more patients associated with the task. For example, if a task involves providing a clinical (or non-clinical) service to a patient, the task attribute information can identify the specific patient involved (e.g., by name, or another patient identifier). For example, the specific patient associated with a task can influence who is assigned to the task based on previous history with the patient and the clinician, based on patient needs and medical history (e.g., identified in the care plan information 240, the clinical order data 242, the EHR data 244, and/or the dynamic patient data 234), based on patient scheduling and availability (e.g., provided in the schedule/availability data 246), based on patient preferences (e.g., provided in the patient preferences data 248 and/or leaned using machine learning techniques), based on patient insurance information 250 and the like). The specific patient associated with a task can also influence when the task is performed and/or where the task is performed based on same or similar criteria/parameters. In some implementations, the patient attributed specific information can also include information regarding a priority status of the patient, including information regarding how the healthcare provider will be reimbursed for the provision for performance of the task (or tasks associated with the patient), such as insurance information and information regarding whether the patient will pay a premium for receiving priority care and/or care in accordance with specified preferences (e.g., regarding time, location and healthcare worker/workers providing the service). In some embodiments, the patient attribute information can specifically identify patient preferences (e.g., determined based on the patient preferences data 248, and/or learned using machine learning techniques) regarding when, where, by whom and/or how (e.g., in person, via telemedicine, food preferences, etc.) a specific task is performed if variable.

The priority attribute information can include attributes that identify or indicate a priority level of a task (e.g., critical/urgent, high priority, low priority, medium priority, etc.). For example, in some implementations, the attribute defining component 312 can determine the priority level of a task based on the priority level being specified in the task definitions/requirement data 202. In some implementations, the timing attributes for a task can be determined based on the priority level associated with a task. For example, tasks classified as high priority can mean that the timing for completion of the task is as soon as possible, while tasks classified as low priority tasks can be assigned at time attribute of "end-of-day."

In some embodiments, the attribute defining component 312 can also associate grouping and/or ordering attributes with two or more tasks regarding the grouping and/or ordering constraints determined by the task grouping component 308 and/or the task ordering component 310. In some embodiments, the attribute defining component 312 can also determine and associate resource attributes with the healthcare tasks that identify or indicate requirements for resources to be used for the tasks, including requirements for healthcare workers authorized to perform the tasks (e.g., determined using the healthcare worker information 204) as well as requirements for non-human resources, such as required medications, medical supplies, devices, equipment, technology and the like for use in association with performing the respective tasks (e.g., determined using the task definitions/requirements data 202 and/or the regulatory information 208).

In one or more embodiments, the task indexing component 316 can organize and index the task information regarding currently pending (and in some implementations forecasted tasks), grouping constraints associated with the tasks, ordering constraints associated with the task, and the various other attributes associated with the respective tasks (e.g., those described herein) to generate indexed task data 112. For example, the indexed task data 112 can include information identifying (e.g., via task identifiers), all healthcare tasks (or a grouped subset) of the healthcare tasks for performance over a defined upcoming timeframe. The indexed task data 112 can further include various relevant attributes associated with each (or in some implementations one or more) indexed task determined by and/or associated therewith by the task grouping component 308, the task ordering component 310, and/or the attribute defining component discussed above. In this regard, the indexed task data can also include or associate various attributes with the tasks that can influence if, where, when, the tasks are performed and by whom.

FIG. 4 presents example indexed task data 400 that can be generated by the task assessment module 108 in accordance with one or more embodiments of the disclosed subject matter. The indexed task data 400 includes various task for performance by healthcare workers of a hospital, referred to herein as hospital A. In the embodiment shown, the indexed task data 400 provides a list of discrete tasks to be performed from a current point in time (e.g., 9:18 am) to defined future point in time (e.g., midnight, or another designated time). The respective tasks are identified by a unique identifier. For example, in accordance with this example, the identifiers can indicate a type of the respective tasks, which include clinical tasks, administrative (admin) tasks, transport tasks, and EVS tasks. For each identified task, if applicable, the indexed task data 400 also identifies the patient associated with the task, the status of the task (e.g., pending or in-progress), a timing constraint associated with the task, a location constraint associated with the task, and a priority level associated with the task. In accordance with this example, the timing attributes can include a timing of origination of the task, a scheduling time constraint associated with the task, and an expected duration the task will take to complete.

With reference again to FIG. 3, the task assessment module 108 can also include task status monitoring component 314 to track information regarding performance of the tasks over a course of operation of the healthcare system. For example, with reference to FIGS. 2 and 3, the task status monitoring component 314 can receive and/or monitor tracked task performance data 226 that identifies or indicates when currently pending tasks are initiated and when they are completed. The task status monitoring component 314 can further regularly and/or continuously update the indexed task data 112 in real-time over the course of operation the integrated healthcare system to reflect changes to the status of the tasks.

Various features and functionalities of the task assessment module 108 involve evaluating dynamic operating data 104 in real-time in view of coinciding static/semi-static system data to identify pending and/or forecasted healthcare tasks (e.g., by the task identification component 304), to determine grouping constraints for two or more of the healthcare tasks (e.g., by the task grouping component 308), to determine ordering constraints for two or more healthcare tasks (e.g., by the task ordering component 310), to determine relevant attributes associated with the healthcare tasks (e.g., by the attribute defining component 312), and/or to determine a status (e.g., currently pending or in-progress) of the healthcare tasks (e.g., by the task status monitoring component 314). In some embodiments, the task assessment module 106 can include task assessment machine learning component 318 to facilitate determining one or more of these task parameters in real-time using various suitable machine learning and/or artificial intelligence (AI)-based schemes.

In some embodiments, these machine learning and/or AI schemes can involve the development, training (e.g., by the task assessment machine learning component 318), and/or application (e.g., by the task identification component 304, the task grouping component 308, the task ordering component 310, etc.) of various machine learning models based on analysis of historical data provided by the one or more healthcare information systems/sources 102 regarding the historical operations of the healthcare system under various dynamic operating conditions/contexts. In this regard, in some embodiments, using various machine learning techniques, the task assessment machine learning component 318 can develop and/or train one or more machine learning models, including one or more task identification models (for application by the task identification component 304) configured to evaluate dynamic operating data 104 in real-time in view of coinciding static/semi-static system data 106 to identify discrete pending and/or forecasted healthcare tasks for assigning to a single healthcare worker or group of healthcare workers. The one or more machine learning models can also include one or more task grouping models (for application by the task grouping component 308) configured to evaluate dynamic operating data 104 in real-time in view of coinciding static/semi-static system data 106 to determine grouping constraints for two or more of the healthcare tasks. The one or more machine learning models can also include one or more task ordering models (for application by the task ordering component 310) configured to evaluate dynamic operating data 104 in real-time in view of coinciding static/semi-static system data 106 and determine ordering constraints for two or more healthcare tasks. The one or more machine learning models can also include one or more attribute extraction models (for application by the attribute defining component 312) configured to evaluate dynamic operating data 104 in real-time in view of coinciding static/semi-static system data 106 to determine relevant attributes associated with the healthcare tasks that can influence scheduling and assignment of resources to the tasks. The one or more machine learning models can also include one or more task status models (for application by the task status monitoring component 314) configured to evaluate dynamic operating data 104 in real-time in view of coinciding static/semi-static system data 106 to determine a status (e.g., currently pending or in-progress) of the healthcare tasks.

For example, the task assessment machine learning component 318 can employ various types of machine learning techniques for learning explicitly or implicitly how segment care plan information into discrete tasks, how to group tasks, and/or how to order tasks via an automatic classification system and process. Inferring or learning can employ a probabilistic or statistical-based analysis to infer an action that is to be executed. For example, in some implementations, a support vector machine (SVM) classifier can be employed. Other learning approaches that can be employed by the task assessment machine learning component 318 can include usage of neural networks (e.g., including deep neural networks, deep adversarial neural networks, convolutional neural networks, and the like), Bayesian networks, decision trees, a nearest neighbor algorithms, boosting algorithm, gradient boosting algorithms, linear regression algorithms, k-means clustering algorithms, association rules algorithms, q-learning algorithms, temporal difference algorithm, and probabilistic classification models providing different patterns of independence can be employed. Learning as used herein also is inclusive of statistical regression that is utilized to develop models of priority.

As will be readily appreciated from the subject specification, the subject innovation can employ learning classifiers that are explicitly trained (e.g., via a generic training data) as well as implicitly trained (e.g., via observing user behavior, receiving extrinsic information) so that the learning classifier is used to automatically determine according to predetermined criteria which action to take. For example, SVM's can be configured via a learning or training phase within a learning classifier constructor and feature selection module. A learning classifier is a function that maps an input attribute vector, k=(k1, k2, k3, k4, kn), to a confidence that the input belongs to a learning class—that is, f(k)=confidence(class).

FIG. 5 presents an example resource assessment module 114 that facilitates determining information regarding availability of resources of an integrated healthcare system in accordance with one or more embodiments of the disclosed subject matter. Repetitive description of like elements employed in respective embodiments is omitted for sake of brevity.

In various exemplary embodiments, the resource assessment module 114 can be configured to determine information regarding the availability of individuals (i.e., the healthcare workers) employed by and/or affiliated with the integrated healthcare system (or an individual operating entity) that can be assigned to the various healthcare tasks for performance by the integrated healthcare system over a defined, upcoming timeframe. In this regard, in addition to knowing what tasks need to be performed, where they need to be performed (if a location constrain is involved), and when they need to be performed (e.g., if a time constraint is involved), in order to determine an optimal scheduling arrangement for the tasks with respect to time and location for performing the respective tasks, the healthcare delivery optimization server device 108 needs to determine who is available to perform the tasks, including when they are or can be available and/or where they are or can be located. With these embodiments, the resource assessment module 114 can determine and/or generate availability information (e.g., resource availability data 116) regarding the availability of the healthcare workers to perform the healthcare tasks (e.g., including currently pending and/or forecasted tasks) to facilitate scheduling and assigning the healthcare workers to the tasks.

For example, in various embodiments, the resource availability data 116 can include information identifying healthcare workers employed by and/or associated with (e.g., as volunteers, independent contractors, patient assistants, etc.) an operating entity or group of operating entities. In some implementations, the identified healthcare workers can be grouped by a suitable aggregation factor. For example, the healthcare workers can be grouped by operating entity, by location, by job/role title, and the like. In another example, the healthcare workers identified can include only those that are "on-the-clock" for the specified defined, upcoming timeframe of interest. In some implementations, the resource availability data 116 can also provide a current (e.g., in real-time or substantially real-time) status of the respective healthcare workers (e.g., available, unavailable, idle, on-task, on-break, etc.). In some implementations, if a worker's current availability status is unavailable (or idle, on-task, on-break, etc.), the resource availability data 116 can include information that identifies or indicates a duration of time until the worker will become available. The resource availability data 116 can also include information identifying or indicating the availability status of the healthcare workers over a defined upcoming timeframe. For example, in implementations in which the healthcare system (or individual operating entity) schedules a healthcare worker to perform certain healthcare tasks at specific times or timeframes in the future (e.g., scheduled patient appointments, scheduled procedures, etc.), the task availability data 116 can include information identifying one or more timeslots in which the healthcare worker is not performing or scheduled to perform a healthcare task. This can include available timeslots identified in the healthcare worker's schedule (e.g., provided in the task scheduling data 218), as well as forecasted available timeslots. The resource availability data 116 can also include location information for the healthcare workers (if applicable) identifying current locations of the respective workers and know or forecasted locations where the workers will be over the defined upcoming timeframe. The resource availability data 116 can also include information regarding a mobility state and/or mode of travel of a worker, such as whether the worker is walking, driving a vehicle, riding as a passenger in a vehicle, flying, etc. In some implementations, the resource availability data 116 can also include information identifying or indicating a current physiological and/or mental state of the healthcare workers, such as a level of fatigue, anxiety, and the like. The resource availability data 116 can also include information regarding healthcare workers that are on-call (e.g., including scheduling information regarding who is on-call and when) or otherwise available if certain criterial is met.

In some embodiments, the resources can also include non-human resources associated with the healthcare tasks, such as supplies, tools, instruments, equipment, technology etc. With these embodiments, the resource availability data 116 can also include information regarding the availability of these non-human resources. For example, the resource availability data 116 can include information identifying the current status of supplies, tools, instruments, equipment, technology etc. (e.g., available, unavailable, broken, dirty, overloaded, low/high bandwidth/power level), the current locations of the supplies, tools, instruments, equipment, etc., the current amount of certain supplies, tools, instruments, equipment, etc., and the like.

FIG. 6 presents example resource availability data 600 that can be generated by the resource assessment module 114 regarding availability of resources of an integrated healthcare system in accordance with one or more embodiments of the disclosed subject matter. The example resource availability data 600 provides current availability information regarding the current availability (e.g., at current time 9:18 am on Apr. 22, 2019) of different healthcare workers at a hospital, hospital A. In the embodiment shown, the different healthcare workers are identified via unique identification (ID) numbers, however the healthcare workers can be identified in various other manners (e.g., by name or the like). The example resource availability data 600 includes information identifying the current availability status of the respective healthcare workers, which in this example is either available, unavailable, or idle. For those healthcare workers that are unavailable or idle, the example resource availability data 600 further identifies an expected duration of time until they will become available. The example resource availability data 600 also includes information identifying an expected duration of time the respective workers will be available (e.g., from 9:18 forward). This can include the expected duration of time in which the available workers will remain available, or the expected duration of time in which the idle or unavailable workers will be available after becoming available. The example resource availability data 600 also includes location information for the respective workers. For example, the location information can identify their current locations, the expected locations at the times they will be available, and/or a start and end destination for certain workers that are currently traveling from one location to another. The example resource availability data 600 can also include mobility state information where appropriate that identifies s a current mobility state of the healthcare workers.

With reference back to FIG. 5, the resource assessment module 114 can include various components to facilitate determining and generating the resource availability data 116, including resource monitoring component 502, resource availability analysis component 510, and resource assessment machine learning component 518.

The resource monitoring component 502 can be configured to extract and/or receive and monitor dynamic operating data 104 provided by the one or more healthcare information systems/sources 102 that provides and/or can be used to determine or infer the resource availability data 116. For example, with respect to healthcare workers, the resource monitoring component 502 can extract, receive and/or monitor information provided by the one or more healthcare information systems/sources 102 regarding what the healthcare workers are doing, where they are located, a physiological and/or mental state of the healthcare workers and the like. In the embodiment shown, the resource monitoring component 502 can include worker activity monitoring component 504 and location tracking component 506.

In various embodiments, the worker activity monitoring component 504 can extract and/or monitor worker activity information regarding what the healthcare workers are doing, including monitoring performance of healthcare tasks scheduled for performance over a defined, upcoming timeframe. The healthcare tasks scheduled for performance can include known tasks pending for performance over the defined, upcoming timeframe, excluding forecasted tasks. For example, the scheduled healthcare tasks can include various tasks assigned to a healthcare worker for performance within the defined timeframe (e.g., a list of tasks to complete, a schedule of patient appointments, etc.). In other implementations, the scheduled healthcare tasks can include unassigned tasks. For example, the scheduled healthcare tasks can include the various discrete healthcare tasks identified by the task identification component 304 for performance of the defined, upcoming timeframe. In this regard, the worker activity monitoring component 504 can extract and/or monitor worker activity information that identifies or can be used to determine when a is currently performing a scheduled task, and/or when the worker will complete the task.

For example, with reference again to FIG. 2, in various embodiments, this information can be provided by one or more task performance task performance tracking systems 224. For example, as described with reference to FIG. 2, in various embodiments, the one or more task performance tracking systems 224 can include a task tracking system that receives user feedback provided the respective healthcare workers reporting what they are doing, including information reporting when they initiate a task and when they complete the task. In some implementations, the task tracking system can also determine and/or provide information tracking the progress of the task to completion (e.g., based on an expected duration of the task and/or based on tracking performance of known actions/steps associated with the task). In some implementations, the task tracking system can also allow workers to provide same or similar feedback for other workers. The one or more task performance tracking systems 224 can include a system that receives and monitors sensory feedback signals capturing information about the activity of the workers using various sensors, including (but not limited to) motion sensors, biofeedback sensors, images, imaging sensors (e.g., live/video, still images) and/or audio sensors. For example, in some implementations, the sensory feedback can be provided by one or more worker monitoring systems 228. The task performance tracking system can further determine what the workers are doing based on the sensory feedback, including whether they are performing a task, what task they are performing and the like. In some embodiments, the task performance tracking system can evaluate this sensory in conjunction with the user provided feedback to facilitate determining what the workers are doing, including determining when the worker reported activity contradicts with the sensory feedback and vice versa. This sensory feedback can also facilitate determining when a worker has idle time, including idle time between tasks and/or during tasks.

The location tracking component 506 can track (e.g., extract/receive and monitor) information regarding the locations and movement of the respective healthcare workers. This can include real-time information regarding current location of the healthcare workers, live movement data regarding movement of the healthcare workers from one location to another, mobility data regarding mode of transportation/movement (e.g., driving, walking, riding as a passenger, etc.), motion data regarding precise body motions of the workers, and the like. For example, in various embodiments, the location tracking component 506 can receive and monitor worker location and movement data provided by one or more worker monitoring systems 226. In some embodiments, the tracked location and movement data (e.g., provided by the worker monitoring systems 228) can be used by the task performance tracking systems in association with the other sensory feedback and/or the user feedback to facilitate determining when a healthcare worker is performing a scheduled task or not, when the healthcare worker will become available and the like (e.g., based on movement in and out of known rooms/buildings/areas, etc. In other embodiments, the resource availability analysis component 510 can evaluate the explicit user feedback regarding what they are doing and when (provided by one or more task performance tracking systems 224), the sensory feedback monitored for the workers (e.g., by the one or more worker monitoring systems 228) and/or the monitored worker location and movement data (e.g., provided by the one or more worker monitoring systems 228) to determine what the healthcare workers are doing (e.g., performing scheduled tasks or not, traveling, etc.) and where they are located over a course of operation of the healthcare system.

The supply tracking component 508 can further extract and/or receive and monitor dynamic operating data 104 regarding the availability and location of supplies, tools, equipment, instruments and the like. In various embodiments, the supply availability data can be provided by and/or determined by one or more operating conditions tracking systems 236. In this regard, the one or more dynamic operating conditions tracking systems 236 can track and provide dynamic operating conditions data 238 regarding the current locations of mobile supplies, instruments and equipment, the status of various supplies, instruments and equipment (e.g., available, unavailable, clean/dirty, broken, in-repair, being delivered, etc.), the available quantities of these resources, and the like.

The resource availability analysis component 510 can be configured to evaluate the information received/extracted and/or monitored by the resource monitoring component 502 to determine and/or infer the resource availability data 116. In one or more embodiments, the resource availability analysis component 510 can include known availability status component 512, forecasted availability status component 514 and idle time component 516. The known availability status component 512 can determine availability information regarding known times or timeframes over a defined upcoming timeframe in which respective healthcare workers are or will be available or unavailable. This can include a current point in time as well as future points/segments in time within the defined, upcoming timeframe. In some embodiments, the known availability status component 512 can determine if a worker is currently performing a task or not (and in some implementations, a specific task) based on current worker activity information extracted/received and/or monitored by the worker activity monitoring component 504. For example, in some implementations, the known availability status component 512 can determine if a worker is currently performing a task or not (and in some implementations, a specific task) based on extracted/received worker activity information including explicit feedback provided by a worker identifying if they are performing a task or not. In other implementations, the known availability status component 512 can also determine if a worker is currently performing a task or not based on learned correlations/patterns in the worker sensory feedback data (e.g., worker motion data, worker biofeedback data, video data, audio data and the like) and/or the worker location data that reflect whether a task (and even a specific task) is being performed or not.

The known availability status component 512 can also employ additional information in combination with explicit worker feedback, worker sensory data and/or worker location/movement data to determine and/or infer whether a worker is currently performing a task or not. For example, this additional information can include scheduling information for the worker (e.g., provided by one or more task scheduling systems 216) identifying tasks the worker is scheduled to perform, timing for performance of the tasks and/or locations for performance of the tasks. This additional information can also include dynamic patient data 234 (e.g., provided by one or more patient monitoring systems 232) identifying current locations and states of patients associated with the scheduled tasks (e.g., if the worker and scheduled patient are at different locations, the scheduled task is probably not being performed unless it is a telemedicine interaction). This additional information can also include information tracked by the supply tracking component 508 regarding availability of supplies to perform certain tasks (e.g., if a required supply is unavailable to perform a scheduled task, it is likely that the healthcare worker is not currently performing the task). The known availability status component 512 can further determine availability information regarding known times or timeframes over a defined upcoming timeframe in which respective healthcare workers are or will be available or unavailable based the scheduling information. The known availability status component 512 can further determine availability information regarding a mobility state and/or mode of travel of a worker, such as whether the worker is walking, driving a vehicle, riding as a passenger in a vehicle, flying, etc., based on the tracked location and/or motion data associated with the worker. The known availability status component 512 can also determine availability information for a worker identifying or indicating a current physiological and/or mental state of the healthcare workers, such as a level of fatigue, anxiety, and the like, based on biofeedback received by one or more worker monitoring systems 228.

The forecasted ability status component 514 can further evaluate the monitored worker activity information and/or the location/movement data in view of known scheduling information for the workers, the indexed task data 112 (including known and forecasted tasks for performance), the dynamic operating conditions data 238, as well as various other types of dynamic and static/semi-static data provided by the healthcare information systems/sources 102) to determine or infer forecasted information regarding worker availability. For example, the forecasted information can include (but is not limited to), expected durations of time until unavailable healthcare works will become available to perform tasks, expected durations of time the available workers will have available when they become available, forecasted timeslots (e.g., including expected point in time and duration) in which workers will be available, forecasted locations where the workers will be available, and the like. In some embodiments, the forecasted availability status component 514 can determine expected times and/or timeslots in which a healthcare worker will be available (or unavailable) based on determining estimated arrival times of the healthcare works to task locations (e.g., using worker location and/or motion tracking information). For example, the forecasted availability status component 514 can determine or infer, based on a worker's current location, distance to a task location, mode of travel, traffic, etc., when a worker can arrive at a task location. According to this example, the travel time/distance can reflect the duration of time until the worker will become available to perform the task.

In one or more additional embodiments, the forecasted availability status component 514 employ one or more machine learning models configured to determine or infer the forecasted resource availability information based on the various parameters monitored by the resource monitoring component 502, the indexed task data 112, dynamic operation conditions data 238 and various additional parameters that have been learned to influence worker availability provided by the healthcare information systems/sources 102. The one or more machine learning models can include but are not limited to: neural networks (e.g., including deep neural networks, deep adversarial neural networks, convolutional neural networks, and the like), Bayesian networks, decision trees, a nearest neighbor algorithms, boosting algorithm, gradient boosting algorithms, linear regression algorithms, k-means clustering algorithms, association rules algorithms, q-learning algorithms, temporal difference algorithm, and probabilistic classification models. In some implementations of these embodiments, the resource assessment module 114 can include resource assessment machine learning component 510 to develop and train the one or more machine learning models based on historical operations data regarding historical availability/unavailability data for the workers (or similar workers) in association with performance of various healthcare tasks under different operating conditions/contexts of the healthcare system. For example, this historical data can include historical data for specific workers regarding their monitored activity in association performing tasks under different operating conditions/context of the healthcare system, including different schedules and scheduled task loads/types of tasks, different occupancy levels, different locations of the tasks, and the like.

The resource availability analysis component 510 can also include idle time component 516 to specifically identify and/or forecast worker idle time in which a healthcare worker can perform supplementary tasks. The term idle time is used herein to broadly refer to one or more segments or periods of time in which a healthcare worker can perform one or more supplementary tasks, such as unscheduled tasks (e.g., tasks on the fly), telemedicine tasks, relatively short tasks, and the like. For example, idle time can include time in which a healthcare worker is between scheduled tasks and/or time in which the healthcare worker can multitask, such as while traveling (e.g., driving, walking, riding as a passenger, etc.), eating lunch, waiting for laboratory results, or the like, that can be utilized to perform supplementary tasks. In various embodiments, the supplementary tasks can include telemedicine tasks, such performing video/telephone chats with patients, remotely monitoring patients, reviewing radiological images, performing remote patient assessments/check-ups, and the like.

With these embodiments, the idle time component 516 can be configured evaluate the information monitored by the resources monitoring component 504 regarding worker activity, worker location and movement data, as well as the various additional types of dynamic operating data 104 and static/semi-static system data 106 described herein (e.g., to identify and/or predict timeframes/segments of idle time in which a healthcare worker can perform a supplementary healthcare task. For example, based on analysis of current activity and scheduling information for a healthcare worker, the idle time component 516 can determine when the healthcare worker will have idle time between scheduled tasks, time in which the worker will be traveling between task locations (e.g., driving, walking, riding as a passenger, etc.), and/or time in which the worker is otherwise being underutilized or can multi-task. In another example, based on analysis of explicit worker feedback indicating the worker is available or has idle time, sensory feedback indicating the worker has idle time, and/or worker motion/movement data, the idle time component 516 can determine that worker currently has N minutes of idle time. For example, the idle time component 516 can determine that a worker has N minutes of idle time while traveling, while eating lunch, while waiting for test results, while no or few patients are being admitted (e.g., idle time of the admittance receptionist, and the like. The idle time component 516 can also employ one or more machine learning techniques to learn and forecast information regarding available idle time, and/or underutilized time of certain healthcare workers based on analysis of historical activity data, travel data, tracked task performance data and the like under different operating contexts/conditions (e.g., regarding scheduling and task load) for the healthcare worker or similar healthcare workers (e.g., with similar job titles, skill levels, location etc.) and different operating conditions/contexts of the healthcare system. In some implementations, these machine learning techniques can involve forecasting upcoming demand and expected time in which the healthcare worker will have to perform a supplementary task given the forecasted demand. In some embodiments, the resource assessment module 114 can also evaluate information regarding current and forecasted demand on system resources (e.g., workers needed, instruments needed, etc.) in view of the resource availability data 116 to determine if and when additional resources need to be activated (e.g., calling in additional workers, brining in additional supplies, etc.). For example, in some implementations of these embodiments, the resource assessment machine learning component 518 can also learn what system resources are needed to satisfy current and/or forecasted system demands. The resource assessment module 114 can further determine if the available resources are sufficient given the current and/or forecasted demand.

FIG. 7 illustrates an example task scheduling and resource assignment optimization module 118 that facilitates coordinating and optimizing resource utilization and delivery of healthcare services across an integrated healthcare system in accordance with one or more embodiments of the disclosed subject matter. In the embodiment shown, task scheduling and resource assignment optimization module 118 can include task optimization analysis component 702 and task assignment component 714. Repetitive description of like elements employed in respective embodiments is omitted for sake of brevity.

The task optimization analysis component 702 can be configured to evaluate the indexed task data 112, the resources availability data 116 and other relevant parameters provided by the one or more healthcare information sources/systems to determine task scheduling and resource assignment information 126 regarding how to schedule tasks and assign resources to the tasks for an integrated healthcare system in real-time in a manner that optimizes performance of the integrated healthcare system as a whole by coordinating, synchronizing and balancing the performance goals of the individual operating entities and the needs and preferences of the patients. In this regard, the task optimization analysis component 702 can evaluate a plurality of complex and dynamic variables for an entire healthcare operating environment (e.g., including a single operating entity or in integrated group of operating entities) regarding what needs to be done and when, who is available to do it, and who is the best person/persons to do it, to determine how to schedule performance of the tasks with respect to time and location and how to assign resources (e.g., workers and optionally non-human resources) to the tasks in a manner that results in performing the tasks in the most efficient and effective manner, using the right resources at the right time for the right patient in the right place.

In various embodiments, the task optimization analysis component 702 can determine how to schedule tasks and assign resources (e.g., healthcare workers, medical supplies, instruments, equipment, etc.) to tasks (e.g., currently pending tasks or scheduled tasks and optimally forecasted tasks) based on task variables provided with the indexed task data 112 (or information provided by the healthcare information systems/sources 102), and resource availability variables provided by the resource viability data 116 (or information provided by the healthcare information systems/sources 102). For example, the task variables or attributes including (but not limited to): task type and/or defined requirements/constraints for a specific task, task location variables (e.g., identifying one more locations for performance of the task, classifying a task location as fixed or variable, identifying whether the task can be performed remotely using telecommunication, identifying patient preferences regarding the task location, identifying start and end locations associated with a task that involves traveling, identifying or indicating a distance associated with the traveling, etc.), task time variables (e.g., identifying or indicated a fixed or variable time or timeframe for completing a task, identifying or indicating an expected duration of the task, etc.), task grouping constraints, task ordering constraints, task priority level, patient preference associated with the tasks (e.g., regarding location, timing, ordering grouping, etc.), and the like. The resource availability variables can include information regarding resource status (e.g., available, unavailable, idle, etc.), known and expected time or timeframes when the resources will be available/unavailable, location and/or movement of the resources, fatigue level, and the like. In some embodiments, the task optimization analysis component 702 can also factor in expected/forecasted need of certain workers, balancing costs associated with assigning them to a certain task now or waiting to assign them to a more demanding or appropriate task expected to arise in the near future The task optimization analysis component 702 can also determine how to schedule tasks and assign healthcare workers to the tasks based on healthcare worker information 204 regarding capabilities, qualifications, preferences, etc., for the respective healthcare workers that can be assigned to the healthcare tasks. For example, with respect to assigning workers to healthcare tasks, in addition to determining who to assign to tasks based on availability of the healthcare workers, the task optimization analysis component 702 can employ worker capability/qualification information to match individual workers with specific tasks that they are capable/qualified to perform. The task optimization analysis component 702 can also examine a pool of available and qualified workers to further assign the "best" workers to the respective tasks in a manner that maximizes utilization of the available workers based on their different qualifications, skill levels, proficiency levels, performance levels, system preference, worker preference, compensation schedule, patient preferences, and the like.

For example, FIG. 8 presents example healthcare worker information 800 (e.g., provided in healthcare worker information 204) that can be applied by the task optimization analysis component 702 to facilitates assigning the healthcare workers to healthcare tasks of an integrated healthcare system in accordance with one or more embodiments of the disclosed subject matter. In accordance with this example, the example healthcare worker information 800 provides task identifiers for the various tasks that the healthcare worker (Dr. Keller), is capable and/or qualified to perform. These tasks include clinical procedure tasks and other clinical tasks, as well as administrative and EVS tasks. In this regard, even though the healthcare worker is a neurological surgeon, the operating entity (e.g., hospital A) can also use the surgeon to perform the noted administrative and EVS tasks when appropriate. The healthcare worker information also includes a system preference rating that indicates the system's preference (e.g., the preference of hospital A or another operating entity associated with hospital A) for using the healthcare worker for the corresponding task and a worker preference rating that indicates the worker's preference for performing the corresponding task (e.g., on a scale of 1-10, wherein 1 is most preferred and 10 is least preferred). The example healthcare worker information 800 also includes a performance rating that reflects the historical performance level of the healthcare worker's performance of the corresponding task. The example healthcare worker information 800 also indicates the workers specific compensation rate for performing the respective tasks.

With reference again to FIG. 7, the task optimization analysis component 702 can employ various machine learning and/or statistical task optimization models/algorithms to facilitate determinizing how to schedule tasks and assign resources to the tasks based on the various parameters/variables described above (e.g., associated with the tasks, the patients associated with the tasks, the healthcare workers that perform the tasks, the non-human resources needed for the tasks, and in some implementations, the forecasted task demand and resource availability). These task optimization models can be configured to determine an optimal task scheduling and resource assignment scheme based on various optimization criteria, including but not limited to: meeting fixed constraints associated with the tasks (e.g., regarding timing, location, resource requirements, ordering constraints, grouping constraints, priority constraints, etc), minimizing delays between performance of the healthcare tasks, ensuring all healthcare tasks are delivered in accordance with defined quality and regulatory requirements, maximizing utilization of available resources, minimizing losses, maximizing revenue, meeting patient preferences with respect to when, where and who performs healthcare tasks, and meeting healthcare worker preferences with respect to preferred tasks, timing and location for perfuming the tasks. In various embodiments, the task optimization analysis component 702 can be configured to employ one or more task optimization models (functions, algorithms, etc.) that determines the optimal task scheduling and resource assignment scheme based on a combination of two or more of these optimization criteria. So for example, assume the healthcare system has a pool of different workers with different capabilities, skill levels, salaries, locations, time availability, schedules, worker preferences, etc. The healthcare system also has many different tasks to be performed by the healthcare workers at any given time or timeframe that vary with respect to type, patient, need, location, time, etc., and wherein new tasks are coming in all the time. In accordance with this example, the task optimization analysis component 702 can employ one or more optimization models that determine how to distribute and assign the tasks to the healthcare workers that results in getting the tasks done as soon as possible, (by a person that is qualified to do it), increases patient quality of care, meets regulatory requirements, minimizes costs (cost attributed to paying workers and complications), maximizes revenue, and the like.

For example, in some implementations, the task optimization analysis component 702 can employ one or more task optimization models that schedules tasks (in terms of timing and location) and assign resources (e.g., in terms of which workers, supplies, etc.) to the tasks in an arraignment that results in minimizing delays between origination of a task and initiation or completion of the task. These task optimization models can thus be configured to schedule tasks with respect to time, location and resources to be used for a task that results in getting the tasks completed as fast as possible, considering fixed constraints (e.g., regarding timing, location, resources, regulatory restrictions, quality control requirements, priority constraints, ordering constraints, etc.) and in some implementations, constraints regarding patient preferences. For example, these task optimization models can favor assigning tasks to healthcare workers that are available now (or the sooner than other healthcare workers) and/or that can travel to the task location in the shortest time, healthcare workers that are historically faster at performing the particular task than other available healthcare worker, and the like.

In another example, the task optimization analysis comment 702 can determine an optimal scheduling arrangement for the respective tasks with respect to timing of performance and location of performance, and who or whom to assign to the respective tasks that results in completing all urgent tasks as soon as possible, completing non-urgent tasks at times and locations preferred by the patients associated with the tasks, meeting defined levels of quality of care and/or regulatory requirements for the tasks, and minimizing costs associated with completing all the tasks.

In other embodiments, the task optimization analysis component 702 can employ one or more task optimization models/functions that schedule tasks (in terms of timing and location) and assign resources (e.g., in terms of which workers, supplies, etc.) to the tasks in an arraignment that results in maximizing utilization of available resources. These resource utilization optimization models can thus be configured to determine, based on the system needs (e.g., the tasks to be performed) how to assign the available healthcare workers in the most efficient and effective manner given the system need and their qualifications/capabilities, locations, etc. For example, in accordance with these embodiments, the one or more task optimization models can be configured to optimize utilization of available resource by minimizing amounts of time in which healthcare workers are not performing tasks, by maximizing the amount of time the healthcare workers perform tasks they are most proficient in, by maximizing revenue, by minimizing losses, etc. In some implementations of these embodiments, the task optimization model can be configured to assign task to healthcare workers to minimize time differences between expected task duration and worker time availability duration with a defined buffer of time for task transitions (which can be based on travel time between task). For example, if a worker has an available timeframe or timeslot of 60 minutes, the task optimization model can be configured to identify and assign a task to the worker for performance within the 60-minute timeslot that has an expected duration of about 55 minutes. In this regard, these task optimization models can be configured to determine the best possible use of all available healthcare workers based on the system and patient needs, considering fixed constraints, patient preferences costs, and the like.

In some embodiments, the task optimization analysis component 702 can employ one or more optimization models that maximize utilization of workers by repurposing uses of the workers in appropriate contexts beyond their primary role and sharing workers across different operating entities based on context and need. With these embodiments, the integrated healthcare system (or individual operating entities) can define all possible types of healthcare tasks each worker can perform based on their qualifications, capabilities, performance level and the like. The healthcare tasks can include healthcare tasks that are traditionally associated with the job title/description, as well as those that are outside of their traditional or primary capacity. For example, the system can identify a set of primary healthcare tasks of a particular surgeon included in the integrated healthcare system, such as the specialized surgery procedures the surgeon is capable of performing. The system can further provide a list of various alternative healthcare tasks the surgeon can perform, including non-surgical tasks, various general clinical tasks traditionally performed by nurses or less specialized clinicians, as well as non-clinical tasks, such as administrative tasks, EVS tasks, and the like. According to these embodiments, the task scheduling and resource assignment optimization module 118 can assign healthcare workers to various types of tasks based on context and need, including tasks that are not their primary role when appropriate to maximize utilization of all workers in every capacity.

In the embodiment shown, the task optimization analysis component 702 includes several components to facilitate determining how to schedule and assign resources to tasks in accordance with one or more optimization models. These components include filtering component 704, task-worker matching component 706, cost analysis component 708, task compensation evaluation component 710 and supplemental task selection component 712.

In various embodiments, the task optimization component 702 can employ the filtering component 704 to facilitate restricting the pool of healthcare workers to assign to pending tasks based on one or more criteria, such as worker capability/requirements and worker availability. For example, in some embodiments, the task optimization analysis component 702 can evaluate information regarding all tasks or a defined subset of task (e.g., grouped by a suitable grouping criterion, such as operating entity, location, priority level, etc.) pending for completion over a defined upcoming timeframe. In some embodiments, the task optimization analysis component 702 can further identify that have not been assigned to a healthcare worker or (or group of healthcare workers) and/or that have otherwise not been scheduled with respect to time, location and/or healthcare worker for performing the task. In this regard, in some embodiments for each "unassigned/unscheduled" tasks, the filtering component 704 can select a subset of the healthcare workers that are qualified/capable to perform the task as determined based on defined capability/qualification restrictions associated with the task and worker capability/quality information associated with the respective workers. The task optimization analysis component 702 can further restrict assignment (e.g., using one or more optimization models) of the healthcare workers to the respective pending tasks based on those subsets of qualified/capable workers to perform the respective tasks and additional criteria/constraints associated with the tasks (e.g., location constraints, time constraints, etc.), the workers (e.g., regarding availability, performance rating, system preferences, worker preferences, etc.), the patients (e.g., patient preferences, and the like). For example, in some implementations in which the defined worker capability information comprises preference classifications for the different types of healthcare tasks representative of relative preference for performance of the different types of healthcare tasks by the respective healthcare workers (e.g., the system preference rating and the worker preference rating information in FIG. 8), the task optimization analysis component 702 can further determine the task assignment scheme using an optimization function that favors assigning healthcare workers to tasks for which they have a higher system and/or worker preference rating as opposed to a lower system and/or worker preference rating.

In another embodiment, the filtering component 704 can evaluate information regarding pending tasks for performance over a defined, upcoming timeframe (e.g., known and/or forecasted) that have not been assigned to healthcare workers. For each identified task, the filtering component 704 can evaluate timing and/or location constraints associated with the task regarding when the task needs to be (or is preferred to be) performed, and/or a location associated with the task. Based on these time/location constraints associated with the task, in some implementations, the filtering component 704 can evaluate availability information for the healthcare workers provided in the resource availability data 116 to identify a subset of available workers that are available to perform. For example, if the task needs to be formed and/or is preferred to be performed now, the filtering component 704 can identify a subset of available workers with immediate availability to perform the task now. In another example, if the task needs to be formed and/or is preferred to be performed now at specific location, the filtering component 104 can identify a subset of workers with immediate availability to perform the task now at the specific location. In another example, if the task needs to be formed and/or is preferred to be performed at specific point in time or over a specific timeframe, the filtering component 704 can identify a subset of available workers with availability to perform the task at the specific point in time or over the specific timeframe. In yet another implementation, if the task is preferred to be performed at specific point in time or over a specific timeframe, the filtering component 704 can identify a subset of available workers with the "best" availability to perform the task at the specific point in time or over the specific timeframe (e.g., workers with the closest availability to perform the task. The task optimization analysis component 702 can further restrict assignment (e.g., using one or more optimization models) of the healthcare workers to the respective pending tasks based on those subsets of available workers to perform the respective tasks and additional criteria/constraints associated with the tasks (e.g., resource requirement constraints, ordering constraints, priority constraints, etc.), the workers (e.g., worker qualifications/performance rating, system preferences, worker preferences, expected need of the workers, etc.), the patients (e.g., patient preferences, and the like). In other embodiments, the filtering component 704 can generate a filtered subset of workers to restrict assigning to task based on filtering the initial pool of healthcare workers by both capability/qualifications criteria and availability criteria.

In another embodiment, the task optimization analysis component 702 can employ task-worker matching component 706 to facilitate matching healthcare workers with task based on the various criteria discussed herein. For example, in various embodiments, the task-worker matching component 706 can dynamically assign a rank or score to different task and healthcare worker combinations for pending and optionally forecasted tasks for performance within a defined upcoming timeframe for a healthcare system based on probability models, inference models, artificial intelligence models, and the like (e.g., a dynamic Bayesian network such as a Hidden Markov Model (HMM) using a Viterbi algorithm and the like). In some implementations, the tasks can be grouped by a suitable grouping criterion (e.g., by operating entity, by location, by timeframe, by priority level, etc.). In this regard, the task-worker matching component 706 can score task-worker assignment combinations to reflect how well the task-worker assignment combination achieves the one or more goals of the system (e.g., meeting fixed constraints, minimizing delay between tasks, optimizing patient flow and care, meeting patient needs and preferences, minimizing costs, maximizing revenue, etc.).

For example, the task-worker matching component 706 can score task-worker assignment options based various criteria, including but not limited to: whether the he worker has the required qualifications/capabilities to perform the task, the specific qualifications held by the worker (e.g., certain tasks can prefer workers with specific qualifications), the system preference rating (e.g., wherein a better preference rating, such a preference rating of 1 is weighed greater than lower preference rating, such as 2), the worker preference rating (e.g., which may hold less weight than the system preference rating, the worker compensation rate for the task (e.g., wherein lower compensation rates are favored over higher compensations rates for certain task to facilitate minimizing costs), and the like. The scoring can also reflect degree of correspondence between worker availability and time/location constraints associated with the task (e.g., providing a measure of how well the worker can fulfil the time constraints based on the worker's availability and current location). In some implementations of these embodiments, the scoring can score the combination based on how close the expected task duration matches the expected worker time availability duration, wherein the lesser the difference the better the score. The scoring can also reflect degree of match between the healthcare worker and preference of the patient associated with the task (e.g., regarding healthcare worker demographics, such as gender, age, language, etc., healthcare worker ratings and review, healthcare worker complication rate, and the like).

The task-worker matching component 706 can thus generate and associate a score with each potential task-worker combination that provides an indication of how well the combination facilitates achieving and/or meeting one or more optimization goals of the healthcare system. The task optimization analysis component can further employ the scores to facilitate determining how to assign the workers to the tasks. For example, in some implementations, the task optimization analysis component 702 can assign the highest scored task-worker combination together. However, in various implementations, the task optimization component 702 can use the scores as additional input to the one or more task optimization models to facilitate task scheduling and assignment. In this regard, the task optimization models can look at all the scores for all the task-worker combinations as a whole in view of various additional parameters associated with coordinating and synchronizing the tasks in terms of timing, location and resources assigned (e.g., a single worker can be matched to two tasks at the same time but not assigned to two tasks at the same time) to determine a final task scheduling and resource assignment scheme that satisfies the one or more optimization criteria of the system.

In another embodiment, the task optimization analysis component 702 can cost analysis component 708 based on costs associated with different optional task scheduling and resource assignment schemes. With these embodiments, the cost analysis component 708 can also evaluate costs associated with different task assignment schemes that assign the one or more healthcare workers to the currently pending tasks in different manners. For example, the costs can include financial costs attributed to time delays, attributed to compensation schemes associated with using certain workers for certain tasks, attributed to expected clinical complications or losses attributed to using certain workers for certain tasks, costs attributed to failure to meet defined regulatory requirements/protocols associated with performing the respective tasks (e.g., by a qualified healthcare worker, in a minimum timeframe, etc.) and the like. The task optimization analysis component 702 can further determine an optimal task scheduling resource assignment scheme based on one or more of the optional task assignments schemes that minimizes the costs. In some implementations of these embodiments, the cost evaluation can involve determining compensation costs associated with using a particular healthcare worker for a certain task. With these implementations, the task compensation evaluation component 710 can determine compensation costs for providing to the healthcare worker if the healthcare worker is assigned to the task based on the task-worker compensation schedule information included in the healthcare worker information 204), and the expected duration of the task, qualification of the healthcare worker, a type of the task, and the like.

In one or more additional embodiments, the task optimization analysis component 702 can include supplemental task selection component 712 to facilitate selecting supplemental task for performance by one or more healthcare workers that have idle time, or that are otherwise not assigned to scheduled/pending tasks. For example, the supplemental task selection component 712 can access one or more supplemental task systems 716 that include supplemental tasks data 718 regarding supplemental task that can be performed by the healthcare workers. For example, the supplemental task can include telemedicine tasks, such performing video/telephone chats with patients, remotely monitoring patients, reviewing radiological images, annotating medical images, performing remote patient assessments/check-ups, and the like. With these embodiments, the supplemental task system 716 can include a telemedicine system with various remote/cloud-based call centers, servers/provider and/or various local provides with one or more physical operating centers.

In this regard, in various implementations, the supplemental task selection component 712 can identify a timeslot for a healthcare worker (e.g., provided in the resource availability data 116) within the defined timeframe in which a healthcare worker of the healthcare workers is not performing or scheduled to perform a healthcare task of the healthcare tasks, and determine a supplemental healthcare task for performance by the healthcare worker during the timeslot. For example, in some implementations, the timeslot can include a timeslot or time segment classified as idle time (e.g., when the healthcare worker is traveling, waiting for lab results, between tasks, eating lunch, etc.). In some implementations in which the timeslot comprises a traveling timeslot over which the healthcare worker will travel from a first location to a second location, the supplemental task component 712 can determine the supplemental task based on a mode the travel. The supplemental task component 712 can also determine the supplemental task based on various other worker-task matching criteria used by the task-worker matching component 706 discussed above.

In some embodiments, the task optimization analysis component 702 can employ several different scheduling and resource assignment schemes for performing healthcare tasks using different optimization models that are targeted to different goals. In this regard, the most efficient and effective manner for scheduling the tasks and assigning resources to the tasks can vary based on the performance goals, needs and preferences of the healthcare system. For example, from the perspective of the operating entity or entities in embodiments in which the disclosed techniques are applied to an integrated healthcare system, the optimal scheduling and resource assignment scheme for all (or a grouped subset) of known tasks to be performed (e.g., within a defined, upcoming timeframe) can be based on achieving and/or balancing one or more of the following goals: minimizing delays between performance of the healthcare tasks, ensuring all healthcare tasks are delivered in accordance with defined quality and regulatory requirements, maximizing utilization of available resources, minimizing losses, maximizing revenue, meeting patient preferences with respect to when, where and who performs healthcare tasks, and meeting healthcare worker preferences with respect preferred tasks, timing and location for perfuming the tasks, and the like.

In this regard, the optimization and/or statistical model or models employed by the task optimization analysis component 702 can be tailored based on the needs and preferences of the specific operating entity and/or integrated healthcare system that employs system 100 to facilitate optimizing their operations. For example, in some implementations, the task optimization analysis component 702 can determine a first task scheduling and resource assignment information 126 using a first optimization model configured to determine an optimal task scheduling and resource assignment scheme that focuses more heavily on minimizing delays between performance of healthcare tasks. The task optimization analysis component 702 can also determine a second task scheduling and resource assignment information 126 using a second optimization model configured to determine an optimal task scheduling and resource assignment scheme using a second optimization model configured to determine an alternative scheme that focuses more heavily on meeting patient preferences. In some embodiments in which the disclosed techniques are applied to an integrated healthcare system including two or more different operating entities, the task optimization analysis component 702 can employ a task optimization model that is configured to balance the needs and preferences of all the different operating entities collectively. For example, the task optimization model can evaluate all indexed task data 112 and resources availability data 116 for the operating entities combined and determine how to schedule and assign resources to the tasks to minimize time total time between task origination can completion collectively for all operating entities, to maximize resource utilization collectively for all entities, etc., With these embodiments, the task optimization model can include a shared resources model in which the resources of all operating entities can be combined and shared, facilitating maximizing resource utilization by coordinating and synchronizing patient and provider needs. In other embodiments, the task optimization analysis component 702 can employ different task optimization models for different operating entities.

The one or more task optimization models can employ various machine learning techniques (e.g., developed based on based on analysis of historical operations data regarding historical performance of various healthcare tasks by the healthcare workers under different operating conditions of the healthcare system) and/or statistical techniques to facilitate determining/inferring the optimal task scheduling and resource assignment information (e.g., SVM classification, neural networks (e.g., including deep neural networks, deep adversarial neural networks, convolutional neural networks, and the like), Bayesian networks, decision trees, a nearest neighbor algorithms, boosting algorithm, gradient boosting algorithms, linear regression algorithms, k-means clustering algorithms, association rules algorithms, q-learning algorithms, temporal difference algorithm, and probabilistic classification models providing different patterns of independence, and the like).

The task assignment component 714 can further generate task scheduling and resource assignment information 126 that can be regularly updated in real-time regarding the determined optimal scheduling/resource assignment scheme or schemes for an operating entity and/or integrated healthcare system. For example, task scheduling and resource assignment information 126 can identify known healthcare task to be performed at a current point in time and/or over a defined upcoming timeframe, and include information identifying a timing for performance of the respective tasks, a location for performance of the respective tasks, the specific healthcare worker or group of healthcare workers assigned to the task, and in some implementations, specific instruments, supplies, equipment, etc., assigned to the respective tasks. The healthcare tasks can include all known healthcare tasks for integrated healthcare system or subsets of the tasks grouped by a defined grouping criterion, such as by operating entity, by location, by patient, by healthcare worker, by timeframe, etc. The task assignment component 714 can further provide the task scheduling and resource assignment information 126 to task management administrators and/or the healthcare workers directly to facilitate performing the healthcare tasks in accordance with the prescribed optimal scheduling and resource assignment scheme.

For example, in some embodiments, the task assignment component 714 can generate and send a task assignment message to a device associated with the healthcare worker comprising information that recommends the healthcare worker perform the supplemental healthcare task during the timeslot. In some implementations, the a task compensation evaluation component 710 can also determine a monetary compensation value for performance of the supplemental healthcare task by the healthcare worker based on a qualification of the healthcare worker, a type of the task, and an expected duration of the task, and the task assignment component 714 can include compensation information with the task assignment message comprises information identifying the monetary compensation value. In other implementation in which the supplemental task comprises a telemedicine service, the task assignment component can include a link associated with the telemedicine service with the task assignment message, wherein selection of the link facilitates performance of the telemedicine service using the device. The task assignment component 714 can also provide the task scheduling and resource assignment information 126 to individual patients to provide a real-time schedule of activities for each patient with anticipated date/time of event and coordinates the sequencing of various activities and services to be rendered (and updated in real-time).

Figure 9:
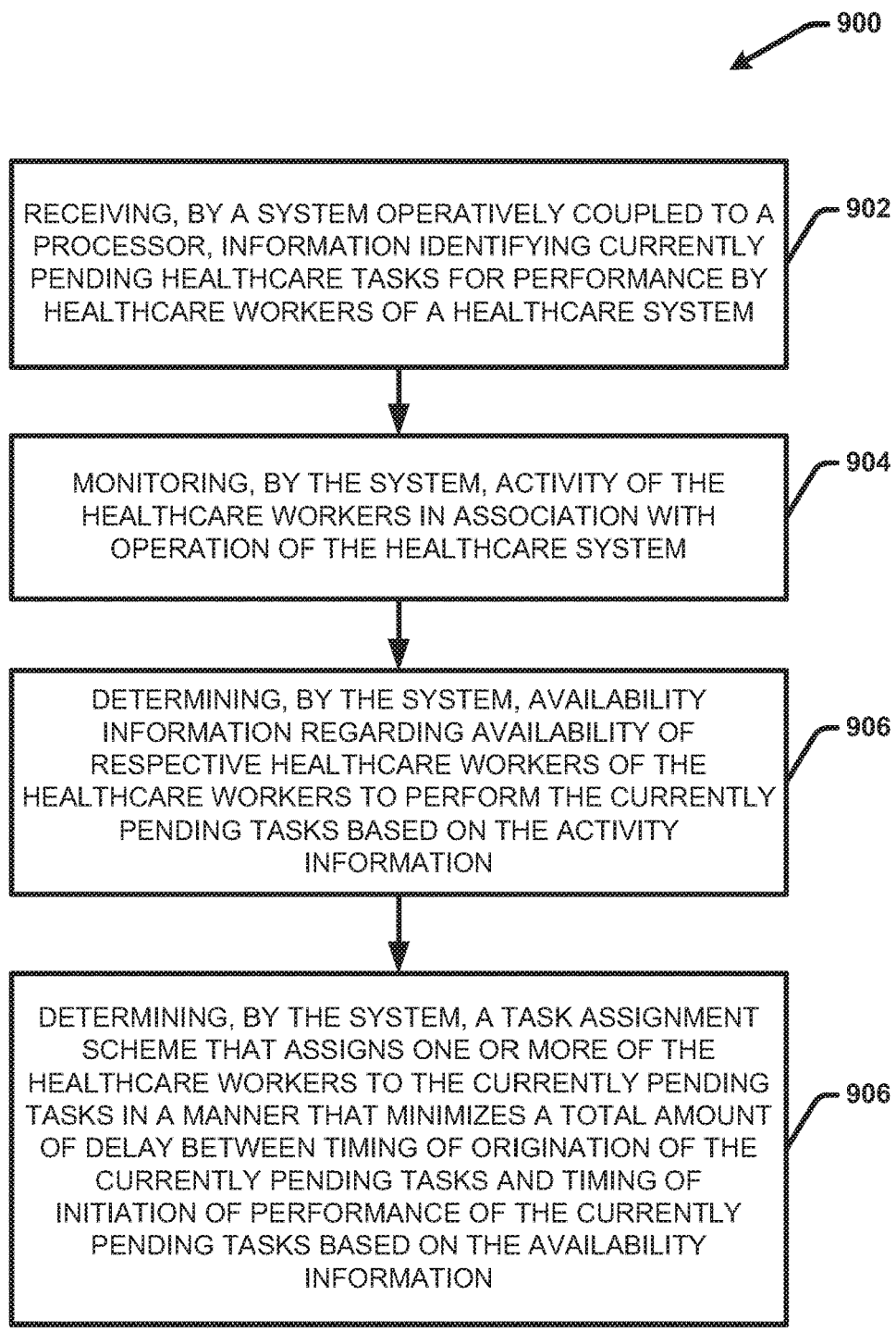
FIG. 9 illustrates an example, high-level flow diagram of a computer-implemented process for coordinating and optimizing resource utilization and delivery of healthcare services across an integrated healthcare system using a machine learning framework, in accordance with one or more embodiments of the disclosed subject matter.

FIG. 9 illustrates an example, high-level flow diagram of a computer-implemented process 900 for coordinating and optimizing resource utilization and delivery of healthcare services across an integrated healthcare system using a machine learning framework, in accordance with one or more embodiments of the disclosed subject matter. Repetitive description of like elements employed in respective embodiments is omitted for sake of brevity.

At 902, a system operatively coupled to a processor (e.g., system 100 or the like), can receive information identifying currently pending healthcare tasks for performance by healthcare workers of a healthcare system (e.g., via task information extraction component 302). At 904, the system can monitor activity of the healthcare workers in association with operation of the healthcare system (e.g., via worker activity monitoring component 504 and location tracking component 506). At 906, the system can determine availability information regarding availability of respective healthcare workers of the healthcare workers to perform the currently pending tasks based on the activity information (e.g., via resource availability analysis component 510). At 906, the system can determine a task assignment scheme that assigns one or more of the healthcare workers to the currently pending tasks in a manner that minimizes a total amount of delay between timing of origination of the currently pending tasks and timing of initiation of performance of the currently pending tasks based on the availability information (e.g., via the task scheduling and resource assignment optimization module 114).

Figure 10:
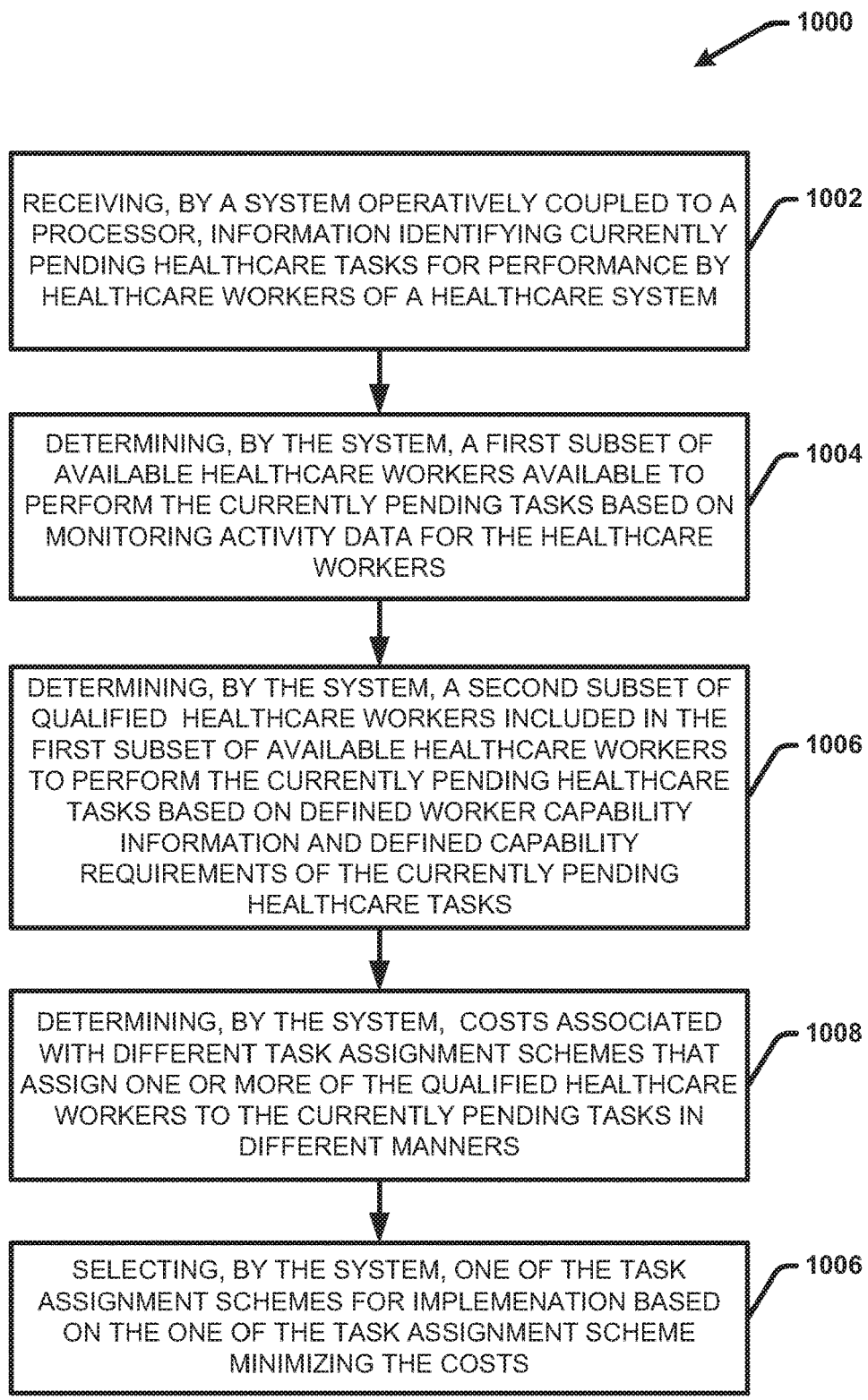
FIG. 10 illustrates another example, high-level flow diagram of a computer-implemented process for coordinating and optimizing resource utilization and delivery of healthcare services across an integrated healthcare system using a machine learning framework, in accordance with one or more embodiments of the disclosed subject matter.

FIG. 10 illustrates another example, high-level flow diagram of a computer-implemented process 1000 for coordinating and optimizing resource utilization and delivery of healthcare services across an integrated healthcare system using a machine learning framework, in accordance with one or more embodiments of the disclosed subject matter. Repetitive description of like elements employed in respective embodiments is omitted for sake of brevity.

At 1002, a system operatively coupled to a processor (e.g., system 100 or the like), can receive information identifying currently pending healthcare tasks for performance by healthcare workers of a healthcare system (e.g., via task information extraction component 302). At 1004, the system can determine a first subset of available healthcare workers of to perform the currently pending healthcare tasks based on monitoring activity data for the healthcare workers (e.g., using worker activity monitoring component 504). At 1006, the system can determine a second subset of qualified healthcare workers included in the first subset of available healthcare workers based on defined worker capability information and defined capability requirements of the currently pending healthcare tasks. At 1008, the system can determine costs associated with different task assignment schemes that assign one or more of the qualified healthcare workers to the currently pending tasks in different manners. At 1010, the system can then select one of the task assignment schemes for implementation based on the one or the task assignment schemes minimizing the costs.

Figure 11:
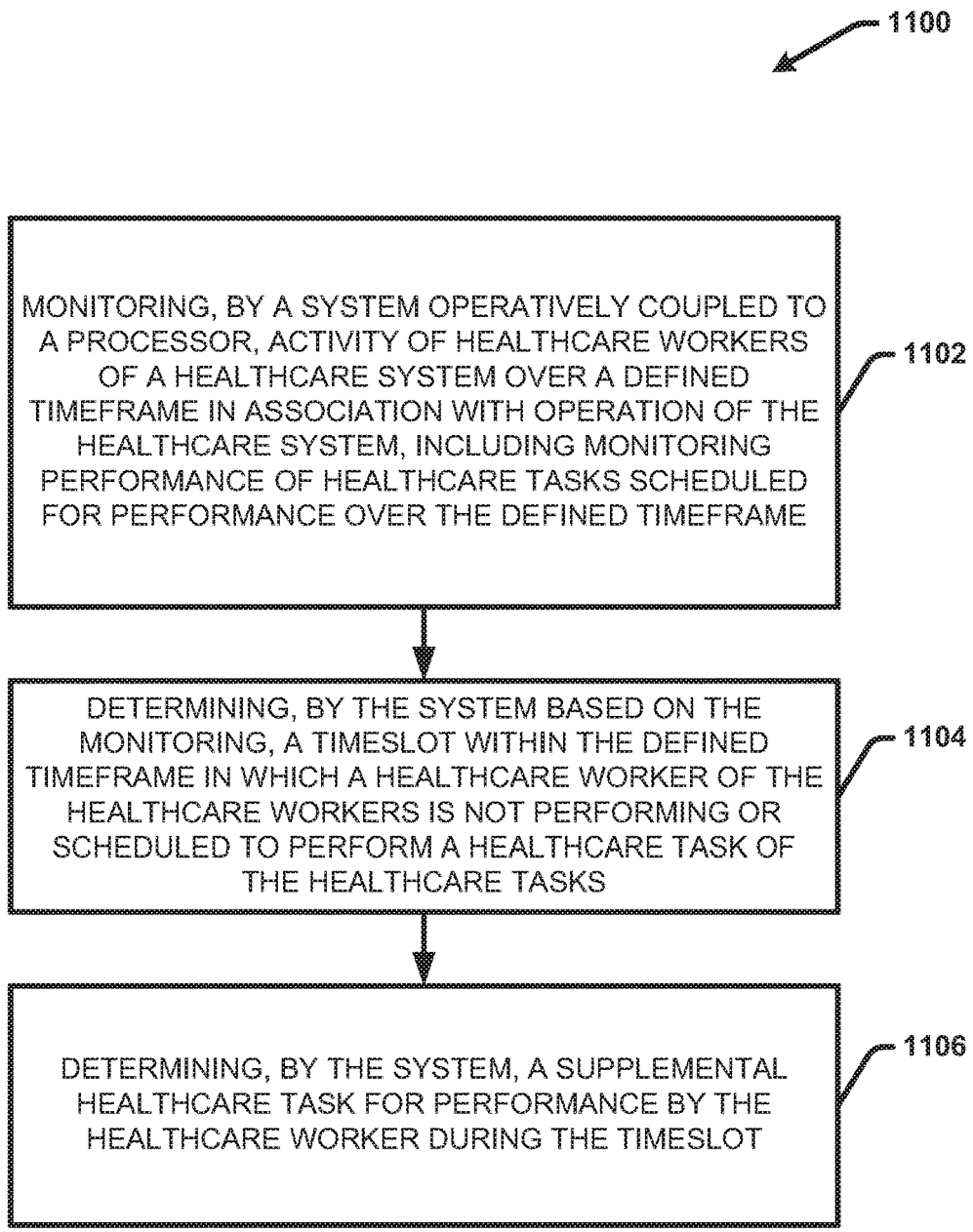
FIG. 11 illustrates another example, high-level flow diagram of a computer-implemented process for coordinating and optimizing resource utilization and delivery of healthcare services across an integrated healthcare system using a machine learning framework, in accordance with one or more embodiments of the disclosed subject matter.

FIG. 11 illustrates another example, high-level flow diagram of a computer-implemented process 1100 for coordinating and optimizing resource utilization and delivery of healthcare services across an integrated healthcare system using a machine learning framework, in accordance with one or more embodiments of the disclosed subject matter. Repetitive description of like elements employed in respective embodiments is omitted for sake of brevity.

At 1102, a system operatively coupled to a processor (e.g., system 100 or the like), can monitor activity of healthcare workers of a healthcare system over a defined timeframe in association with operation of the healthcare system, including monitoring performance of healthcare tasks scheduled for performance over the defined timeframe (e.g., using worker activity monitoring component 504). At 1104, the system can determine, based on the monitoring, a timeslot within the defined timeframe in which a healthcare worker of the healthcare workers is not performing or scheduled to perform a healthcare task of the healthcare tasks (e.g., using resource availability analysis component 510). At 1106, the system can further determine a supplemental healthcare task for performance by the healthcare worker during the timeslot (e.g., using task scheduling and resource assignment optimization module 114).

Figure 12:
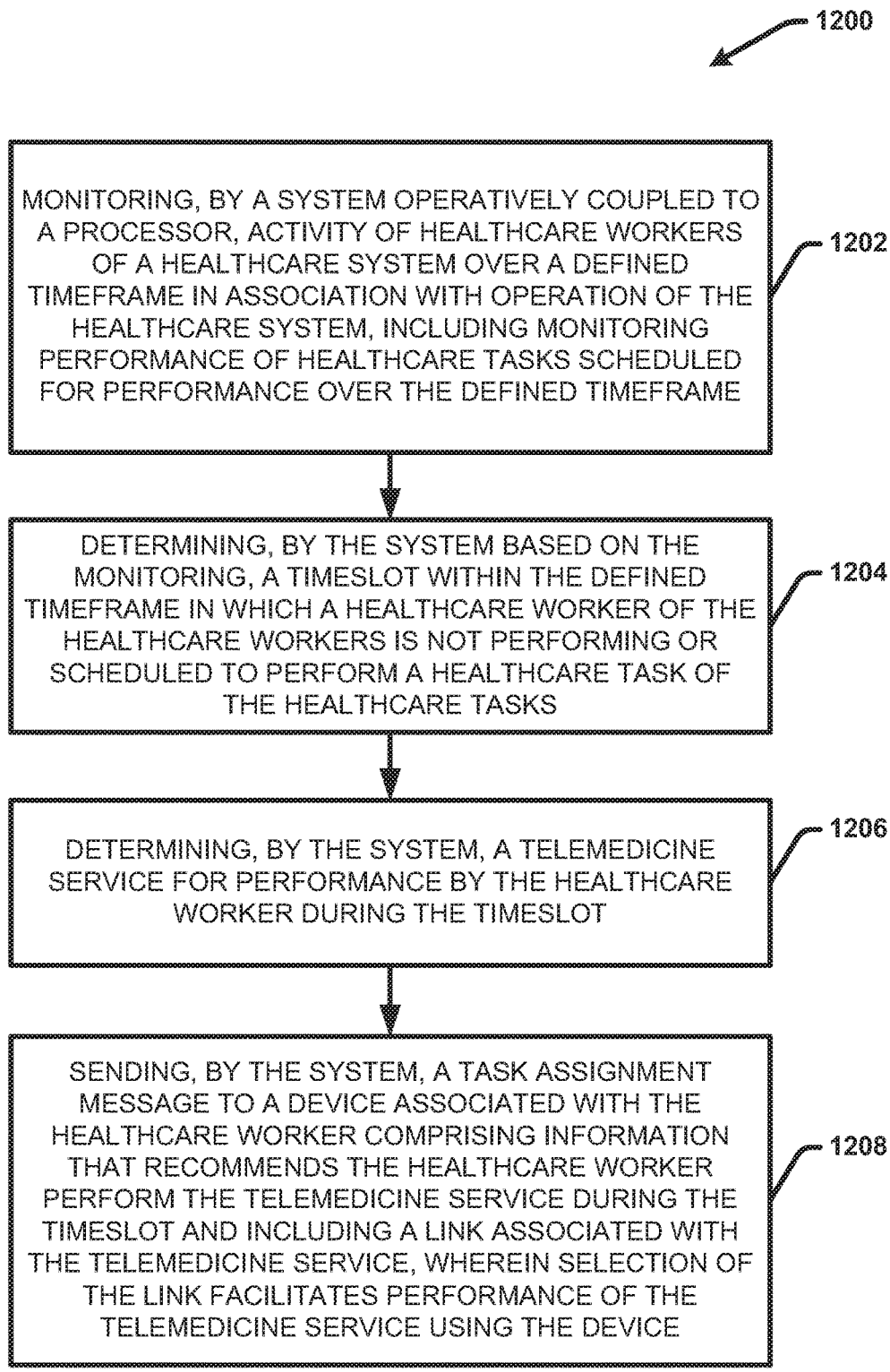
FIG. 12 illustrates another example, high-level flow diagram of a computer-implemented process for coordinating and optimizing resource utilization and delivery of healthcare services across an integrated healthcare system using a machine learning framework, in accordance with one or more embodiments of the disclosed subject matter.

FIG. 12 illustrates another example, high-level flow diagram of a computer-implemented process 1200 for coordinating and optimizing resource utilization and delivery of healthcare services across an integrated healthcare system using a machine learning framework, in accordance with one or more embodiments of the disclosed subject matter. Repetitive description of like elements employed in respective embodiments is omitted for sake of brevity.

At 1202, a system operatively coupled to a processor (e.g., system 100 or the like), can monitor activity of healthcare workers of a healthcare system over a defined timeframe in association with operation of the healthcare system, including monitoring performance of healthcare tasks scheduled for performance over the defined timeframe (e.g., using worker activity monitoring component 504). At 1204, the system can determine, based on the monitoring, a timeslot within the defined timeframe in which a healthcare worker of the healthcare workers is not performing or scheduled to perform a healthcare task of the healthcare tasks (e.g., using resource availability analysis component 510). At 1206, the system can determine a telemedicine service for performance by the healthcare worker during the timeslot. At 1208, the system can further send a task assignment message to a device associated with the healthcare worker comprising information that recommends the healthcare worker perform the telemedicine service during the timeslot and including a link associated with the telemedicine service, wherein selection of the link facilitates performance of the telemedicine service using the device (e.g., using task scheduling and resource assignment optimization module 114).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 13:
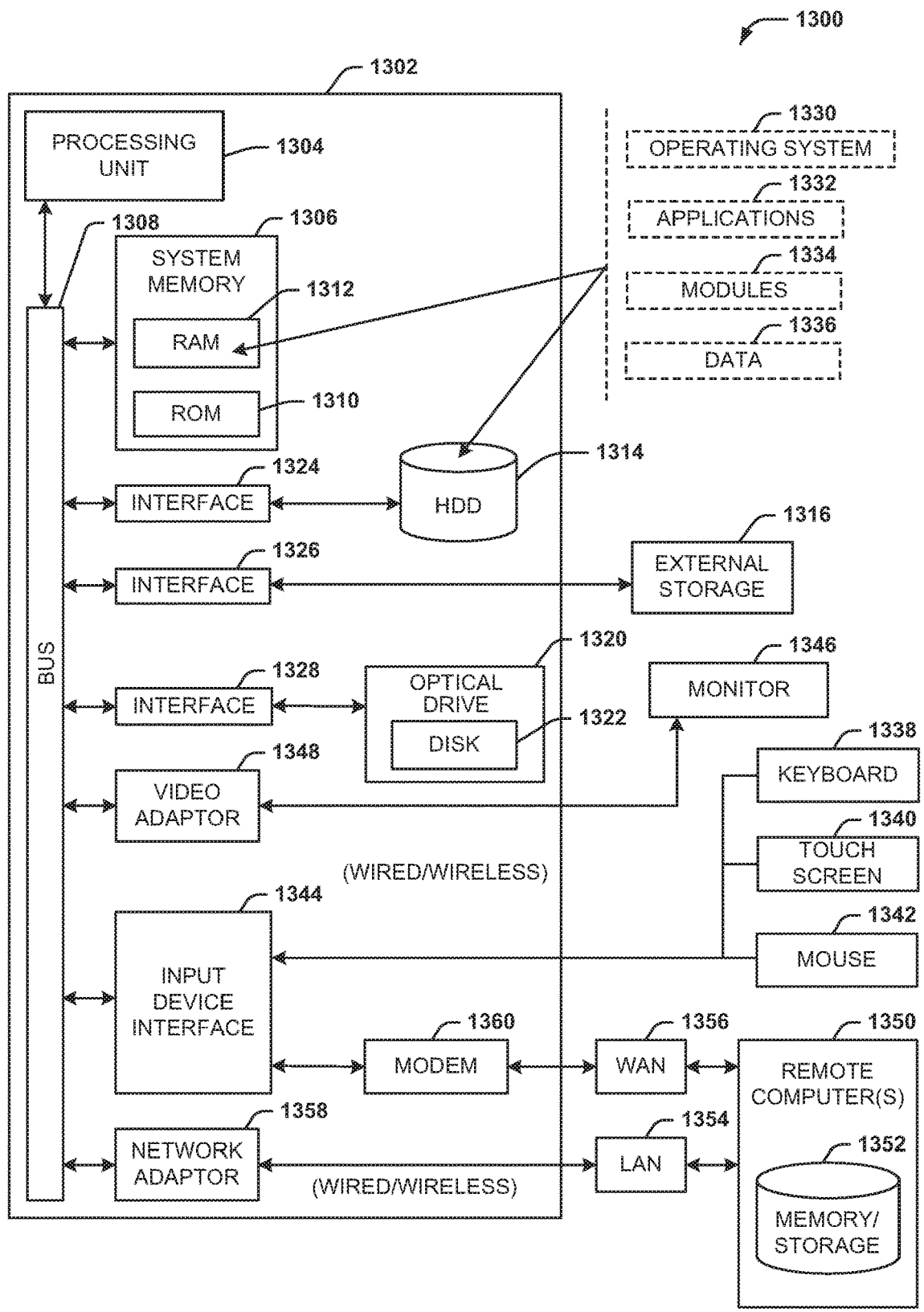
FIG. 13 illustrates a block diagram of an example, non-limiting operating environment in which one or more embodiments described herein can be facilitated.

In order to provide additional context for various embodiments described herein, FIG. 13 and the following discussion are intended to provide a brief, general description of a suitable computing environment 1300 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 13, the example environment 1300 for implementing various embodiments of the aspects described herein includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures can also be employed as the processing unit 1304.

The system bus 1308 can be any of several types of bus structure that can further interconnect to a memory bus (with or without a memory controller), a peripheral bus, and a local bus using any of a variety of commercially available bus architectures. The system memory 1306 includes ROM 1310 and RAM 1312. A basic input/output system (BIOS) can be stored in a non-volatile memory such as ROM, erasable programmable read only memory (EPROM), EEPROM, which BIOS contains the basic routines that help to transfer information between elements within the computer 1302, such as during startup. The RAM 1312 can also include a high-speed RAM such as static RAM for caching data.

The computer 1302 further includes an internal hard disk drive (HDD) 1314 (e.g., EIDE, SATA), one or more external storage devices 1316 (e.g., a magnetic floppy disk drive (FDD) 1316, a memory stick or flash drive reader, a memory card reader, etc.) and an optical disk drive 1320 (e.g., which can read or write from a CD-ROM disc, a DVD, a BD, etc.). While the internal HDD 1314 is illustrated as located within the computer 1302, the internal HDD 1314 can also be configured for external use in a suitable chassis (not shown). Additionally, while not shown in environment 1300, a solid state drive (SSD) could be used in addition to, or in place of, an HDD 1314. The HDD 1314, external storage device(s) 1316 and optical disk drive 1320 can be connected to the system bus 1308 by an HDD interface 1324, an external storage interface 1326 and an optical drive interface 1328, respectively. The interface 1324 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1302, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1312, including an operating system 1330, one or more application programs 1332, other program modules 1334 and program data 1336. All or portions of the operating system, applications, modules, and/or data can also be cached in the RAM 1312. The systems and methods described herein can be implemented utilizing various commercially available operating systems or combinations of operating systems.

Computer 1302 can optionally comprise emulation technologies. For example, a hypervisor (not shown) or other intermediary can emulate a hardware environment for operating system 1330, and the emulated hardware can optionally be different from the hardware illustrated in FIG. 13. In such an embodiment, operating system 1330 can comprise one virtual machine (VM) of multiple VMs hosted at computer 1302. Furthermore, operating system 1330 can provide runtime environments, such as the Java runtime environment or the .NET framework, for applications 1332. Runtime environments are consistent execution environments that allow applications 1332 to run on any operating system that includes the runtime environment. Similarly, operating system 1330 can support containers, and applications 1332 can be in the form of containers, which are lightweight, standalone, executable packages of software that include, e.g., code, runtime, system tools, system libraries and settings for an application.

Further, computer 1302 can be enable with a security module, such as a trusted processing module (TPM). For instance with a TPM, boot components hash next in time boot components, and wait for a match of results to secured values, before loading a next boot component. This process can take place at any layer in the code execution stack of computer 1302, e.g., applied at the application execution level or at the operating system (OS) kernel level, thereby enabling security at any level of code execution.

A user can enter commands and information into the computer 1302 through one or more wired/wireless input devices, e.g., a keyboard 1338, a touch screen 1340, and a pointing device, such as a mouse 1342. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1304 through an input device interface 1344 that can be coupled to the system bus 1308, but can be connected by other interfaces, such as a parallel port, an IEEE 1394 serial port, a game port, a USB port, an IR interface, a BLUETOOTH® interface, etc.

A monitor 1346 or other type of display device can be also connected to the system bus 1308 via an interface, such as a video adapter 1348. In addition to the monitor 1346, a computer typically includes other peripheral output devices (not shown), such as speakers, printers, etc.

The computer 1302 can operate in a networked environment using logical connections via wired and/or wireless communications to one or more remote computers, such as a remote computer(s) 1350. The remote computer(s) 1350 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1352 is illustrated. The logical connections depicted include wired/wireless connectivity to a local area network (LAN) 1354 and/or larger networks, e.g., a wide area network (WAN) 1356. Such LAN and WAN networking environments are commonplace in offices and companies, and facilitate enterprise-wide computer networks, such as intranets, all of which can connect to a global communications network, e.g., the Internet.

When used in a LAN networking environment, the computer 1302 can be connected to the local network 1354 through a wired and/or wireless communication network interface or adapter 1358. The adapter 1358 can facilitate wired or wireless communication to the LAN 1354, which can also include a wireless access point (AP) disposed thereon for communicating with the adapter 1358 in a wireless mode.

When used in a WAN networking environment, the computer 1302 can include a modem 1360 or can be connected to a communications server on the WAN 1356 via other means for establishing communications over the WAN 1356, such as by way of the Internet. The modem 1360, which can be internal or external and a wired or wireless device, can be connected to the system bus 1308 via the input device interface 1344. In a networked environment, program modules depicted relative to the computer 1302 or portions thereof, can be stored in the remote memory/storage device 1352. It will be appreciated that the network connections shown are example and other means of establishing a communications link between the computers can be used.

When used in either a LAN or WAN networking environment, the computer 1302 can access cloud storage systems or other network-based storage systems in addition to, or in place of, external storage devices 1316 as described above. Generally, a connection between the computer 1302 and a cloud storage system can be established over a LAN 1354 or WAN 1356 e.g., by the adapter 1358 or modem 1360, respectively. Upon connecting the computer 1302 to an associated cloud storage system, the external storage interface 1326 can, with the aid of the adapter 1358 and/or modem 1360, manage storage provided by the cloud storage system as it would other types of external storage. For instance, the external storage interface 1326 can be configured to provide access to cloud storage sources as if those sources were physically connected to the computer 1302.

The computer 1302 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
     an activity monitoring component that monitors activity information regarding real-time activity of healthcare workers of a healthcare system over a defined timeframe in association with operation of the healthcare system, the activity information including task information regarding performance of scheduled healthcare tasks scheduled for performance over the defined timeframe;
     an availability analysis component that employs one or more first machine learning processes to forecast, based on the activity information and historical operations data regarding historical performance of various healthcare tasks by the healthcare workers under different operating conditions of the healthcare system, a timeslot within the defined timeframe in which a healthcare worker of the healthcare workers will not be performing a scheduled healthcare task of the scheduled healthcare tasks;
     a task optimization analysis component that determines a supplemental healthcare task for performance by the healthcare worker during the timeslot based on identification of the timeslot; and
     a task assignment component that facilitates assigning the supplemental healthcare task to the healthcare worker during the timeslot based on determining the supplemental healthcare task.

2. The system of claim 1, wherein based on determining the supplemental healthcare task, the task assignment component that generates and sends a task assignment request message to the device comprising information that requests the healthcare worker perform the supplemental healthcare task during the timeslot, and wherein the task assignment component assigns the supplemental healthcare task to the healthcare worker based on reception of an acceptance message from the device accepting assignment of the supplemental task in response to the task assignment request message.

3. The system of claim 2, wherein the computer executable components further comprise:
   a task compensation evaluation component that determines a monetary compensation value for performance of the supplemental healthcare task by the healthcare worker based on a qualification of the healthcare worker, a type of the supplemental task, and an expected duration of the supplemental task, and wherein the task assignment message request message comprises information identifying the monetary compensation value.

4. The system of claim 2, wherein the supplemental task comprises a telemedicine service, and wherein the task assignment component includes a link associated with the telemedicine service in the task assignment request message, wherein selection of the link facilitates performance of the telemedicine service using the device during the timeslot.

5. The system of claim 1, wherein the computer executable components further comprise:
   a location tracking component that receives location and movement data regarding locations and movement of the healthcare workers in real-time over the defined timeframe, and wherein the task monitoring component further forecasts the timeslot based on the location and movement data.

6. The system of claim 1, wherein the timeslot comprises a traveling timeslot over which the healthcare worker will travel from a first location to a second location, and wherein the task optimization analysis component determines the supplemental task based on a mode the travel.

7. The system of claim 1, wherein the availability analysis component further infers, based on the activity information and using one or more second machine learning processes, one or more segments of idle time associated with a current healthcare task of the healthcare tasks that is currently being performed by the healthcare worker, and wherein the task optimization analysis component further determines another supplemental healthcare task for performance by the healthcare worker during the one or more segments of idle time.

8. The system of claim 1, wherein the task optimization analysis component determines the supplemental healthcare task using one or more second machine learning processes based on a time and duration of the timeslot, defined task capabilities of the healthcare worker, a location of the healthcare worker, a fatigue level of the healthcare worker, a mobility state of the healthcare worker, one or more preference of the healthcare worker, a current operating context of the healthcare system, and the historical operations data.

9. The system of claim 1, wherein the task optimization analysis component determines the supplemental healthcare task based on a time and duration of the timeslot, defined task capabilities of the healthcare worker, a location of the healthcare worker, a fatigue level of the healthcare worker, a mobility state of the healthcare worker, one or more preferences of the healthcare worker, and a current operating context of the healthcare system.

10. The system of claim 1, wherein the supplemental healthcare task involves provision of healthcare to a patient, and wherein the task optimization analysis component determines the supplemental healthcare task for performance by the healthcare worker based on one or more preferences of the patient and availability of the patient.

11. The system of claim 10, wherein the optimization analysis component determines the patient preferences and the availability of the patient using one or more machine learning optimization models configured to infer the patient preferences and availability based on analysis of historical operations data regarding historical performance of various healthcare tasks by the healthcare workers under different operating conditions of the healthcare system.

12. The system of claim 1, wherein the task optimization analysis component further determines the supplemental healthcare task based on defined task capabilities of the healthcare worker at the healthcare system, pending supplemental healthcare tasks for performance at the healthcare system, and defined capability requirements for the supplemental healthcare tasks.

13. The system of claim 12, wherein the defined task capabilities identifies a task preference hierarchy of different types of tasks the healthcare worker is capable of performing at the healthcare system, and wherein the task optimization component further determines the supplemental healthcare task based on the task preference hierarchy and using an optimization function that favors selection of higher ranked pending supplemental healthcare tasks in the task preference hierarchy over lower ranked pending supplemental healthcare tasks in the task preference hierarchy.

14. The system of claim 1, wherein the healthcare system defines one or more primary tasks for performance by the healthcare worker at the healthcare system based on a primary role of the healthcare worker at the healthcare system, and secondary tasks for performance by the healthcare worker at the healthcare system associated with one or more secondary healthcare worker roles at the healthcare system, and wherein the task optimization analysis component selects the supplemental task from the one or more secondary tasks.

15. A method comprising:
monitoring, by a system operatively coupled to a processor, activity information regarding real-time activity of healthcare workers of a healthcare system over a defined timeframe in association with operation of the healthcare system, the activity information including monitring task information regarding performance of scheduled healthcare tasks scheduled for performance over the defined timeframe;
forecasting, by the system, a timeslot within the defined timeframe in which a healthcare worker of the healthcare workers will not be performing a scheduled healthcare task of the scheduled healthcare tasks based on the activity information using one or more first machine learning processes and historical operations data regarding historical performance of various healthcare tasks by the healthcare workers under different operating conditions of the healthcare system; and
determining, by the system based on identification of the timeslot, a supplemental healthcare task for performance by the healthcare worker during the timeslot; and
based on the determining, facilitating, by the system, assignment of the supplemental healthcare task to the healthcare worker during the timeslot.

16. The method of claim 15, wherein the facilitating comprises:
sending, by the system, a task assignment request message to the comprising information that requests the healthcare worker perform the supplemental healthcare task during the timeslot; and
assigning, by the system, the supplemental healthcare task to the healthcare worker based on reception of an acceptance message from the device accepting assignment of the supplemental task in response to the task assignment request message.

17. The method of claim 16, further comprising:
determining, by the system, a monetary compensation value for performance of the supplemental healthcare task by the healthcare worker based on a qualification of the healthcare worker, a type of the task, and an expected duration of the task; and
including, by the system, information identifying the monetary compensation value in the task assignment request message.

18. The method of claim 16, wherein the supplemental task comprises a telemedicine service, and wherein the method further comprises:
including, by the system, a link associated with the telemedicine service in the task assignment request message, wherein selection of the link facilitates performance of the telemedicine service using the device.

19. The method of claim 16, wherein the determining the supplemental healthcare task comprises determining the supplemental healthcare task using one or more second machine learning processes based on a time and duration of the timeslot, defined task capabilities of the healthcare worker, a location of the healthcare worker, a fatigue level of the healthcare worker, a mobility state of the healthcare worker, one or more preference of the healthcare worker, a current operating context of the healthcare system, and the historical operations data.

20. A non-transitory machine-readable storage medium, comprising executable instructions that, when executed by a processor, facilitate performance of operations, comprising:
monitoring activity information regarding real-time activity of healthcare workers of a healthcare system over a defined timeframe in association with operation of the healthcare system, the activity information including task information regarding performance of scheduled healthcare tasks scheduled for performance over the defined timeframe;
forecasting a timeslot within the defined timeframe in which a healthcare worker of the healthcare workers will not be performing a scheduled healthcare task of the scheduled healthcare tasks based on the activity information using one or more first machine learning processes and historical operations data regarding historical performance of various healthcare tasks by the healthcare workers under different operating conditions of the healthcare system;
determining, based on identification of the timeslot, a supplemental healthcare task for performance by the healthcare worker during the timeslot; and
based on the determining, facilitating assignment of the supplemental healthcare task to the healthcare worker during the timeslot.

\* \* \* \* \*